United States Patent
Hanina et al.

(10) Patent No.: US 9,361,562 B1
(45) Date of Patent: Jun. 7, 2016

(54) METHOD AND APPARATUS FOR FRACTAL MULTILAYERED MEDICATION IDENTIFICATION, AUTHENTICATION AND ADHERENCE MONITORING

(71) Applicant: Ai Cure Technologies, Inc., New York, NY (US)

(72) Inventors: Adam Hanina, New York, NY (US); Yaniv Ganor, Brookline, MA (US); Maurice Lepouttre, Brooklyn, NY (US); Christian Wolf, New Rochelle, NY (US)

(73) Assignee: Ai Cure Technologies, Inc., New York, NY (US)

( * ) Notice: Subject to any disclaimer, the term of this patent is extended or adjusted under 35 U.S.C. 154(b) by 0 days.

(21) Appl. No.: 13/837,687

(22) Filed: Mar. 15, 2013

Related U.S. Application Data

(63) Continuation-in-part of application No. 13/646,634, filed on Oct. 5, 2012, now abandoned, and a continuation-in-part of application No. 13/338,602, filed on Dec. 28, 2011, now Pat. No. 8,720,790.

(60) Provisional application No. 61/750,217, filed on Jan. 8, 2013, provisional application No. 61/623,148, filed on Apr. 12, 2012, provisional application No. 61/623,193, filed on Apr. 12, 2012, provisional application No. 61/683,849, filed on Aug. 16, 2012, provisional application No. 61/544,056, filed on Oct. 6, 2011.

(51) Int. Cl.
| | | |
|---|---|---|
| G06K 19/06 | (2006.01) | |
| B41J 2/01 | (2006.01) | |
| G06K 7/14 | (2006.01) | |
| G06F 17/00 | (2006.01) | |
| G06T 7/00 | (2006.01) | |
| G06F 19/00 | (2011.01) | |
| G06K 9/62 | (2006.01) | |

(52) U.S. Cl.
CPC ........ G06K 19/06037 (2013.01); G06K 7/1408 (2013.01); *G06F 17/00* (2013.01); *G06F 19/321* (2013.01); *G06K 9/6203* (2013.01); *G06T 7/0012* (2013.01); *G06T 7/0014* (2013.01)

(58) Field of Classification Search
USPC .............. 347/107, 101, 110, 2; 235/494, 375; 382/128; 348/164
See application file for complete search history.

(56) References Cited

U.S. PATENT DOCUMENTS

| | | | |
|---|---|---|---|
| 4,728,783 A | | 3/1988 | Brass et al. |
| 4,941,193 A | * | 7/1990 | Barnsley et al. .............. 382/249 |

(Continued)

OTHER PUBLICATIONS

Kiani, et al., *A New Method of Fractal Barcodes Identification*, Proceedings of the World Congress on Engineering and Computer Science, vol. 1, Oct. 19-21, San Francisco, USA (2011).

(Continued)

*Primary Examiner* — Julian Huffman
*Assistant Examiner* — Leonard S Liang
(74) *Attorney, Agent, or Firm* — Fish & Richardson P.C.

(57) ABSTRACT

A method and system for authenticating medication. The method includes the steps of printing a first recoverable key on a medication pill, printing a second recoverable key on a medication packaging for the medication pill, employing at least a portion of the first recoverable key to extract information from the second recoverable key, and providing medication authentication in accordance with information extracted from the second recoverable key. The first recoverable key and the second recoverable key may include one or more fractal properties.

23 Claims, 21 Drawing Sheets

(56) References Cited

U.S. PATENT DOCUMENTS

| | | | | |
|---|---|---|---|---|
| 5,065,447 | A | * | 11/1991 | Barnsley et al. ............... 382/249 |
| 5,347,600 | A | * | 9/1994 | Barnsley ................ G06T 9/001 375/E7.204 |
| 5,384,867 | A | * | 1/1995 | Barnsley et al. ............... 382/249 |
| 5,416,856 | A | * | 5/1995 | Jacobs et al. .................. 382/249 |
| 5,430,812 | A | * | 7/1995 | Barnsley et al. ............... 382/235 |
| 5,845,264 | A | * | 12/1998 | Nellhaus ........................ 705/28 |
| 5,992,742 | A | * | 11/1999 | Sullivan et al. .......... 235/462.01 |
| 5,995,673 | A | * | 11/1999 | Ibenthal et al. ............... 382/249 |
| 6,002,794 | A | * | 12/1999 | Bonneau et al. ............. 382/166 |
| 6,229,931 | B1 | * | 5/2001 | Essafi et al. .................. 382/305 |
| 6,661,904 | B1 | * | 12/2003 | Sasich et al. ................. 382/100 |
| 6,674,875 | B1 | * | 1/2004 | Phillips et al. ............... 382/100 |
| 6,799,725 | B1 | * | 10/2004 | Hess et al. ............... 235/462.01 |
| 7,059,526 | B1 | * | 6/2006 | Sullivan et al. .......... 235/462.01 |
| 7,152,206 | B1 | | 12/2006 | Tsuruta |
| 7,304,228 | B2 | | 12/2007 | Bryden et al. |
| 7,619,819 | B2 | * | 11/2009 | Moon et al. ................... 359/569 |
| 8,422,792 | B2 | * | 4/2013 | Kruglick ....................... 382/199 |
| 2004/0034579 | A1 | | 2/2004 | Xu et al. |
| 2007/0152032 | A1 | * | 7/2007 | Tuschel et al. ................ 235/375 |
| 2007/0152056 | A1 | * | 7/2007 | Tuschel et al. ................ 235/454 |
| 2007/0194034 | A1 | | 8/2007 | Vasiadis |
| 2008/0106726 | A1 | | 5/2008 | Park |
| 2008/0138604 | A1 | * | 6/2008 | Kenney et al. ................ 428/323 |
| 2008/0290168 | A1 | | 11/2008 | Sullivan et al. |
| 2011/0091068 | A1 | * | 4/2011 | Stuck et al. ................... 382/103 |
| 2011/0186629 | A1 | * | 8/2011 | Stuck et al. ................... 235/380 |
| 2013/0084249 | A1 | * | 4/2013 | Lawandy ..................... 424/10.2 |
| 2013/0088555 | A1 | * | 4/2013 | Hanina et al. ................. 347/107 |
| 2013/0127959 | A1 | * | 5/2013 | Hanina ......................... 347/101 |

OTHER PUBLICATIONS

Kiani, et al., *A Multi-Purpose Digital Image Watermarking Using Fractal Block Coding*; Journal of Systems and Software, vol. 84, Issue 9, pp. 1550-1562 (Sep. 2011) (Abstract only).

Kiani, et al., *A Fractal Based Image Watermarking for Authentication and Verification*, Image and Signal Processing, CISP 2009, Oct. 17-19, 2009 (Abstract only).

PCT Search Report and Written Opinion, in PCT/US2012/059139 (Dec. 18, 2012) (7 pages).

* cited by examiner a) Initial Set     b) 1 Iteration     c) 2 Iterations     d) 3 Iterations a) Initial Set     b) 1 Iteration     c) 2 Iterations     d) 3 Iterations a) Initial Set     b) 1 Iteration     c) 2 Iterations     d) 3 iterations a) Initial Set     b) 1 Iteration     c) 2 Iterations     d) 3 iterations a) Cantor1   b) Cantor2   c) Cantor3 a) Image of a Cantor code in an ellipse
b) Output of Canny edge detector
c) Lines detected by the Hough transform
d) Potential squares a) The best-matching square            b) Segmented Cantor code ready for scanning a) Segmented Cantor code    b) Edge image of segmented Cantor code a) Incorrect affine transformation        b) Close-up of 1st quadrant c) Correct affine transformation        d) Close-up of 1st quadrant

METHOD AND APPARATUS FOR FRACTAL MULTILAYERED MEDICATION IDENTIFICATION, AUTHENTICATION AND ADHERENCE MONITORING

CROSS REFERENCE TO RELATED APPLICATIONS

This application claims the benefit of and incorporates by reference the entire contents of U.S. Provisional Patent Application Ser. No. 61/750,217, titled Method and apparatus for Fractal Multilayered Medication Identification, Authentication and Adherence Monitoring, filed Jan. 8, 2013 to Hanina at al. This application is also a continuation-in-part of U.S. patent application Ser. No. 13/646,634, titled Method and Apparatus for Fractal Identification, filed Oct. 5, 2012 to Hanina et al., which is in turn a continuation-in-part of U.S. patent application Ser. No. 13/388,602, titled Method and Apparatus for Fractal Identification, filed Dec. 28, 2011 to Hanina, and the entire contents of each of these applications being incorporated herein by reference. The '634 applications in turn claims the benefit of U.S. Provisional Patent Application Ser. No. 61/544,056, titled Method and Apparatus for Fractal Identification, filed Oct. 6, 2011 to Hanina, the entire contents thereof being incorporated herein by reference. The '602 application in turn claims the benefit of U.S. Provisional Patent Application Ser. No. 61/623,148, titled Method and Apparatus for Fractal-ID™—Fractal Identification and Verification System, filed Apr. 12, 2012 to Hanina et al; U.S. Provisional Patent Application Ser. No. 61/623,193, titled Method and Apparatus for Fractal-ID™—L-System Fractal Curve Identification, filed Apr. 12, 2012 to Hanina et al.; and U.S. Provisional Patent Application Ser. No. 61/683,849, titled Method and Apparatus for Identification, filed Aug. 16, 2012 to Hanina et al., the contents of these applications being incorporated herein by reference.

STATEMENT REGARDING FEDERALLY SPONSORED RESEARCH OR DEVELOPMENT

This invention was made with government support under grant number 1R43TR000190-01 awarded by National Center for Advancing Translational Sciences, National Institutes of Health. The Government has certain rights in the invention.

TECHNICAL FIELD

This application relates generally to the identification and authentication of products, and more particularly to the identification and authentication of medication such as medication pills or other medication, and more particularly to the identification and authentication of such medication using fractal encoded images in a multilayered schema. The invention relates generally to any situation in which a multi-step in general, and two-step in particular, identification and authentication process may be employed for any product, object or the like.

BACKGROUND

Counterfeit Medication

A counterfeit medication or a counterfeit drug is a medication or pharmaceutical product which is produced and sold with the intent to deceptively represent its origin, authenticity or effectiveness. A counterfeit drug may contain inappropriate quantities of active ingredients or none at all, may be improperly processed within the body (e.g., absorption by the body), may contain ingredients that are not on the label (which may or may not be harmful), or may be supplied with inaccurate or fake packaging and labeling. Counterfeit medicinal drugs include those with less or none of the stated active ingredients, with added, sometimes hazardous, adulterants, substituted ingredients, completely misrepresented, or sold with a false brand name. Otherwise legitimate drugs that have passed their date of expiry are sometimes remarked with false dates. Low-quality counterfeit medication may cause any of several dangerous health consequences including side effects, allergic reactions, in addition to their obvious lack of efficacy due to having less or none of their active ingredients. Medicines which are deliberately mislabeled in order to deceive consumers—including mislabeled but otherwise genuine generic drugs—are counterfeit.

Since counterfeiting is difficult to detect, investigate, quantify, or stop, the quantity of counterfeit medication is difficult to determine. Counterfeiting occurs throughout the world, although there are claims that it is more common in some developing countries with weak regulatory or enforcement regimes. It is estimated that more than 10% of drugs worldwide are counterfeit, and in some countries more than 50% of the drug supply is counterfeit. In 2003, the World Health Organization estimated that the annual earnings of counterfeit drugs were over US $32 billion.

The considerable difference between the cost of manufacturing counterfeit medication and price that counterfeiters charge is a lucrative incentive. Fake antibiotics with a low concentration of the active ingredients can do damage worldwide by stimulating the development of drug resistance in surviving bacteria. Courses of antibiotic treatment which are not completed can be dangerous or even life threatening. If a low potency counterfeit drug is involved, completion of a course of treatment cannot be fully effective. Counterfeit drugs have even been known to have been involved in clinical drug trials.

Medication Identification

In addition to the problem with counterfeit medications, simple identification of medication is also an extremely large problem. More than 80% of adults in the U.S. take at least one pill a week, whether prescription, OTC, vitamin or herbal. Yet the pills they are taking are difficult to identify based on their visual characteristics alone. Pill identification, or the inability to correctly visually identify a pill, is a large contributing factor to medication errors. These errors can occur anywhere along the drug-taking process. Difficulty with pill identification is further exacerbated when patients are older, have some form of impairment, take multiple drugs or have limited health literacy. 1.5 million people are harmed each year because of medication errors. The cost of treating drug-related injuries in hospitals is approximately $3.5 billion per year. The actual number of medication errors is presumably much higher since not all medication errors lead to injury or death. A pill's poor labeling and packaging are thought to cause one third of medication errors, while studies have also shown that a pill's shape and color are important factors in drug identification.

Existing Identification and Anti-Counterfeiting Technologies

There are several technologies that have been employed in an effort to combat the counterfeit drug problem, and to allow for identification of medication. A review of these technologies is provided below in Table 1 (the final column comprising features associated with elements of the present invention).

TABLE 1

|  | Overt | Covert | Forensic | Track & Trace | | Invention |
|---|---|---|---|---|---|---|
|  | Visible Marking | Invisible ink | Taggants | Barcode ID | RFID |  |
| Technology | Optical | Optical | Chem/Phys | Optical | Electronic | Optical |
| Data reading method | Visual | Imaging | Lab | Imaging | RF/Magnetic | Imaging |
| Reading range | Short | Short | N/A | Short | Long | Short |
| Line of sight | Needed | Needed | N/A | Needed | Not needed | Needed |
| Occlusion immunity |  |  |  |  | + | + |
| Medication information | + | + | + | + | + | + |
| Supply chain mapping |  |  |  | + | + | + |
| Data privacy |  | + | + | + |  | + |
| Identification capability | + | + | + | + | + | + |
| Pill specific information |  |  |  | + |  | + |
| Authentication capability* |  |  | + |  |  | + |
| Counterfeit resistance* |  |  |  |  |  | + |
| Adherence monitoring |  |  |  |  |  | + |
| Cost | Low | High | High | Low | High | Low |

*The unique authentication capability and counterfeit resistance of the system of the present invention stems from the high geometrical complexity and self-similarity of fractals, combined with the multilayered data verification process As can be seen from Table 1, such existing technologies include visible markings, invisible ink markings, chemical/physical taggants, barcoding and RFID tagging. While each of these technologies has its benefits and limitations, the solution presented in accordance with the various embodiments of the invention (and as set forth in the rightmost column in Table 1, and thus is considered part of the invention and not a presentation of merely background material) provides a beneficial combination of price, ease of use, precision and robustness.

An example of one of the technologies described in Table 1 is radio frequency identification (RFID) which uses electronic devices to track and identify items, such as pharmaceutical products, by assigning individual serial numbers to the containers holding each product. The U.S. Food and Drug Administration (FDA) is working towards an Electronic pedigree (ePedigree) system to track drugs from factory to pharmacy. This technology may prevent the diversion or counterfeiting of drugs by allowing wholesalers and pharmacists to determine the identity and dosage of individual products. Some techniques, such as Raman spectroscopy and Energy Dispersive X-Ray Diffraction (EDXR) can be used to discover counterfeit drugs while still inside their packaging. Other more traditional systems may be applied to such medication identification, such as barcoding being provided on medication packaging (either one or two dimensional). For such a use, however, any damage to the barcode, difficulty in printing the barcode (such as deformation based upon printing surface), or obscuring a portion of the barcode may render the barcode inoperative.

Marking individual pills with one or more identifiers is considered a useful method for identification, but has been traditionally thought of being cost prohibitive while offering only minimal improvement over packaging marking. One or more barcodes may be employed (either one or two dimensional) and may be printed to individual medication pills, instead of, or in addition to, being printed to the medication packaging. Such a printing process may be implemented by employing one or more appropriate printing apparatuses, such as a pad printing apparatus provided by Printing International® N.V./S.A., for example. Thus, each pill may be individually printed with the use of such a pad printing apparatus. Laser marking has also been used to print high-resolution images or barcodes directly onto pills. In consumable products, Mars®, Inc. utilizes inkjet or pad printers to print images cheaply onto individual pieces of candy. Indeed, U.S. Pat. No. 7,311,045 describes a system for printing multi color images on a candy by maintaining a directional registration of the candy between printing steps. In each instance, holding each individual medication pill or candy is performed by vacuuming the pieces in place, and holding the piece firmly in place between steps so that orientation of the piece during printing does not change. Other patents and applications assigned to Mars®, Inc. describe a number of systems and methods for printing food grade inks onto shaped candy elements.

While one or two dimensional barcodes have been used to serialize individual pills and verify authenticity and identity, but as recognized by the inventors of the present invention, their designs are relatively easy to replicate, require fixed surface areas and specific alignment for printing, and are rendered unusable if occlusion occurs due to handling or if the barcode is damaged. Unlike forensic features, which are embedded into an item, in barcode technology the item's physical attributes are completely distinct from the barcode itself. Further, whether using such a pad printing process, or employing other printing methods such as ink jet printing or laser marking for imparting markings to candy or medication pills, the inventors of the present invention have recognized that the need for purposefully handling individual pills may be time consuming and expensive. Further, the described printed elements may fail to provide robust images sufficient to act as a unique identifier for a particular batch of processed elements. For such a use, as noted, any damage to the barcode, difficulty in printing the barcode (such as deformation based upon printing surface), or obscuring a portion of the barcode may render the barcode inoperative. Traditional barcodes similarly may not be able to handle being printed on uneven surfaces where substantial noise may be generated by changes to the barcode from the printing surface, such as on a medication pill or the like. Additionally, barcodes may be easily copied and applied to counterfeit objects. None of these systems are sufficient for imparting robust identification information to a pill or other candy object.

There therefore currently exists no easy and reliable way to identify and authenticate medication pills. The widespread problem of counterfeit drugs and the huge number of medication errors within the health system are in large part due to an inability to correctly identify a medication pill. The packaging and labeling around a drug is no guarantee of authenticity. Trying to identify a pill based on its physical characteristics or imprint is almost impossible for the average consumer or healthcare worker.

Therefore, it would be desirable to provide a method and apparatus that overcome the drawbacks of the prior art.

SUMMARY

In accordance with one or more embodiments of the present invention, a universal secure labeling system for individual medication pills and capsules is provided, and in particular may comprise a system and method for using a plurality of fractal encoded images in a multilayered approach.

The inventors of the present invention have determined that two main methods of prescription medication packaging exist: a) Pills in a blister-pack and a box; and b) Loose pills in a container, re-packed in the pharmacy. Therefore, in accordance with various embodiments of the present invention, principles of fractal-based, medication identification and authentication, addressing both packaging methods, are presented.

The high geometrical complexity and self-similarity of fractals, combined with a multilayered data verification process, hold a potential for an efficient and highly reliable method that will significantly reduce the number of medication errors and remove counterfeit drugs from the marketplace. Furthermore, these same features also provide a high level of copying resistance because the inherent complexity on the proposed solution makes it difficult to copy with high accuracy and precision.

The inventors of the present invention provide herein a number of methods for generating fractal-based medication identification images, and recovering information therefrom. Each of the number of methods is preferably used at one or more different steps in the process. Indeed, any desirable combination of these images may be employed in the noted identification and authentication process.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

The detailed embodiments of the invention will now be described making reference to the following drawings in which like reference numbers denote like structure or steps. Furthermore, while the invention is described as applying to medication pills in one or more types of containers, the invention should be considered applicable to any situation in which such a two-step identification and authentication process may be employed, and may indeed be employed to protect any product or the like. Of course a greater number of identification steps may be employed, as well as a single step employing a single barcode. Finally, each of the fractal identification image generation descriptions may be used to generate such an image at any time, and need not necessarily be tied to the use with an identification system as described herein.

Medication Authentication and Identification Schemes

The inventors of the present invention have determined that medication is generally packaged in two manners. First, medication pills may be provided individually packaged in a blister pack inside a box, and second, the medication pills may be provided loosely inside a container. While the methods are similar, the inventors of the present invention have determined that somewhat different identification and authentication methods would be appropriate for the different situations.

In a situation where the medication pills are distributed in blister packages in a box, the medication is preferably dispensed from the factory via one or more conduits, such as a pharmacist or the like. Because there is no interaction at an individual pill level by the pharmacist, the inventors of the present invention have determined that both identification and authentication may preferably be performed by an end user of the medication. In accordance with a first embodiment of the invention, identification and authentication mechanisms preferably comprise two linked layers, Layer L1 comprising a pill layer, and Layer L2 comprising a box layer. L2, or other layer codes, may also be provided to the user via a hang tag, into a pharmacy card or other identification, thus resulting in a permanent key for a user, or may be provided in conjunction with a prescription or the like, either electronically, such as to the phone of the user, other mobile device, email, etc. Additionally, various biometric data may be provided as a portion of one or more of the codes, and may be used in conjunction therewith.

Figure 1:
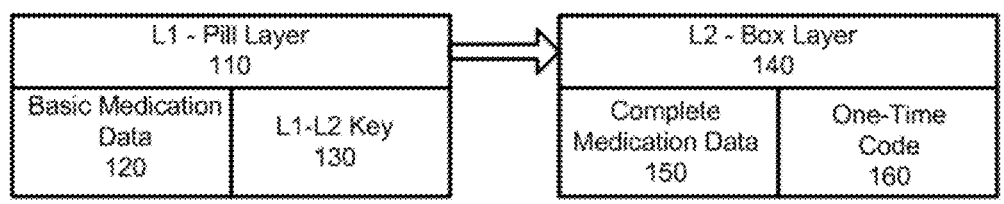
FIG. 1 depicts a first key combination in accordance with an embodiment of the invention.

For each layer, it is contemplated in accordance with the various embodiments of the invention to include a data-encoded fractal image including various medication information encoded therein (and in particular the use of one or more of the fractal images described below may be employed, although the scheme is applicable to the use of any image, fractal or not). The more precise format of such fractal images will be described below. As is shown in FIG. 1, a fractal image in accordance with an embodiment of the invention to be used in accordance with Pill layer L1 110 preferably may include information describing basic medication data 120 and an L1-L2 Key 130. The basic medication data group may contain basic medication identification data needed at time of consumption, to prevent erroneous medication selection, and may include one or more of medication name, dosage strength and other relevant information. L1-L2 key 130 may contain at least in part a code needed to read and correlate between the basic medication data on the pill and a presentation of substantially complete (or other desirable) medication data on the box (as will be next described), and to read any one-time code therefrom needed for medication authentication.

A fractal image in accordance with an embodiment of the invention to be used in accordance with the Box Layer L2 140 preferably may include information describing complete medication information 150 and a one-time code 160 to be used for authenticating the medication. As noted above, preferably information from L1-L2 key 130 may be employed in order to properly read one time code 160. The complete medication data group of information preferably contains all (or a portion of) the data necessary to unequivocally identify the medication and all its parameters. This information may typically be accessed one-time only when opening a new medication box. This information may preferably comprise one or more of the following: Product information (medication name, dosage strength, expiration date); Manufacturing information (location, date, batch/lot); Distribution information (country/state, distributor, wholesaler, chain, etc.); Usage information (instructions on how to use the medication, side effects, other medication information typically contained in a medication insert; and the like.

One-time code 160 may be preferably used for medication authentication. Since it is practically impossible for a given box to contain both genuine and counterfeited medication, this information may be accessed one time only upon opening a new medication box. Every single medication box may preferably have a different one-time code. One-time code 160 may expire after being sent to an identification and authentication computer, or other appropriate location for identification and authentication. One time code 160 is preferably linked to a specific medication (through the need for L1-L2 key 130 for access thereto), it may prevent the use of a one-time code of a low-price medication (if bought by a counterfeiter) to be exploited for high-price medication, or other misappropriation of the code.

Figure 2:
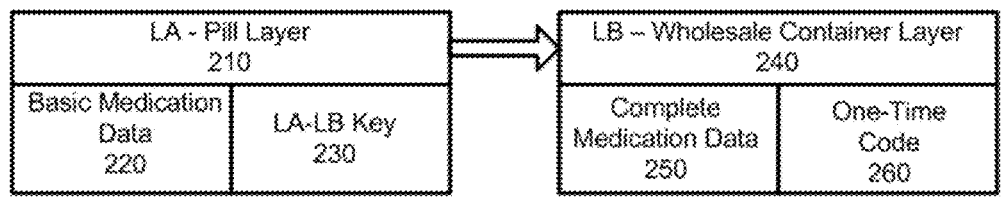
FIG. 2 depicts a second key combination in accordance with an embodiment of the invention.

In an alternative situation where the medication pills are distributed loosely in a pill container, the medication is preferably dispensed from the factory in a bulk fashion, and then provided into smaller containers for use by individuals by a pharmacist or the like. In this situation, in accordance with the various embodiments of the invention, it may be preferable to perform both identification and authentication of the medication by the pharmacist or other repackager using the wholesale container, and again perform identification of the medication by the end user. Therefore, as is shown in FIG. 2, and in accordance with a second embodiment of the invention, identification and authentication mechanisms preferably comprise two linked layers, Layer LA 210 comprising a pill layer, and Layer LB 240 comprising a wholesale container layer.

For each layer, it is contemplated in accordance with the various embodiments of the invention to include a data-encoded fractal image including various medication information encoded therein. The more precise format of such fractal images will be described below. A fractal image in accordance with an embodiment of the invention to be used in accordance with Pill layer LA 210 preferably may include information describing basic medication data 220 and an LA-LB key 230. Basic medication data 220 may contain basic medication identification data needed at time of consumption, to prevent erroneous medication selection, and may include one or more of medication name, dosage strength and other relevant information. LA-LB key 230 may contain at least in part a code needed to read and correlate between the basic medication data on the pill and a presentation of substantially complete (or other desirable) medication data on the wholesale container (as will be next described), and to read any one-time code therefrom needed for medication authentication.

A fractal image (or other image sharing one or more characteristics with fractal images) in accordance with an embodiment of the invention to be used in accordance with the Wholesale Container Layer LB 240 preferably may include information describing complete medication information 250 and a one-time code 260 to be used for authenticating the medication. As noted above, preferably information from LA-LB key 230 may be employed in order to properly read this one time code. Complete medication data 250 group of information preferably contains all (or a portion of) the data necessary to unequivocally identify the medication and all its parameters. This information will typically be accessed one-time only when opening a new wholesale medication container. This information may preferably comprise one or more of the following: a) Product information (medication name, dosage strength, expiration date); b) Manufacturing information (location, date, batch/lot); c) Distribution information (country/state, distributor, wholesaler, chain, etc.); and the like.

One-time code 260 may be used for medication authentication. Since it is practically impossible for a given wholesale container to contain both genuine and counterfeited medication, this information may preferably be accessed one-time only upon opening a new wholesale container of medication. Every single wholesale medication container may preferably have a different one-time code. One-time code 260 preferably expires after being sent to an identification and authentication computer, or other appropriate location for identification and authentication. Since one-time code 260 is preferably linked to a specific medication (through the need for LA-LB key 230 for access thereto), it may prevent the use of a one-time code of a low-price medication (if bought by a counterfeiter) to be exploited for high-price medication, or other misappropriation of the code.

Once the above process has been performed by the receiver of the wholesale container, the medication pills are preferably then provided to an end user of the medication in a retail medication container. It is further anticipated that the end user may employ a further medication identification step, as will now be described. In accordance with this embodiment of the invention, Pill Layer LA 210 is preferably the same as in the preceding process employing the wholesale container, while a different retail container Layer LC 340 is preferably provided as a fractal image on the retail medication container.

For each layer, it is contemplated in accordance with the various embodiments of the invention to include a data-encoded fractal image including various medication information encoded therein. The more precise format of such fractal images will be described below. A fractal image in accordance with an embodiment of the invention to be used in accordance with Pill Layer LA 210 (as described above) preferably may include information describing basic medication data and an LA-LC key 330. (The LA-LC key 330 information may be the same or different from LA-LB key 230 information described above) Basic medication data 220 may contain basic medication identification data needed at time of consumption, to prevent erroneous medication selection, and may include one or more of medication name, dosage strength and other relevant information, as noted above. LA-LC key 330 may contain at least in part a code needed to read and correlate between the basic medication data on the pill and a presentation of complete medication data on the retail medication container (as will be next described), and to read any one-time code therefrom needed for medication authentication.

A fractal image in accordance with an embodiment of the invention to be used in accordance with the Retail Container Layer LC 340 preferably may include information describing complete medication information 350. As authentication has already taken place at the wholesale level, no further authentication is necessary at this point, and therefore a one-time key to be used for authenticating the medication need not be provided in accordance with the retail medication container (although such may be provided if an extra level of security is desired). The complete medication data 350 group of information preferably contains all (or a portion of) the data necessary to unequivocally identify the medication and all its parameters. This information will typically be accessed one-time only when opening a new retail medication container. This information may preferably comprise one or more of the following: a) Product information (medication name, dosage strength, expiration date); b) Manufacturing information (location, date, batch/lot); c) Distribution information (country/state, distributor, wholesaler, chain, etc.); and the like.

System Use

Figure 4:
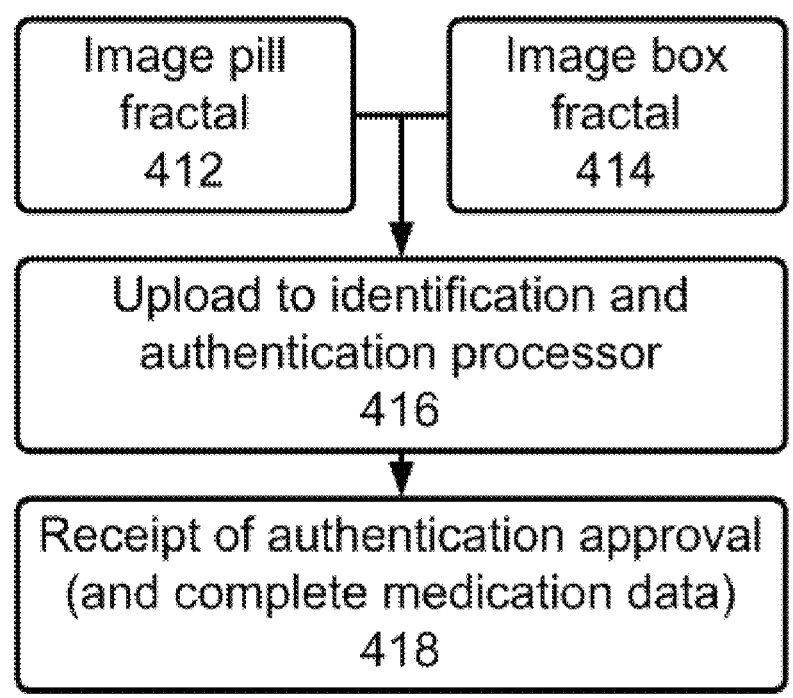
FIG. 4 depicts a medication authentication sequence in accordance with an embodiment of the invention.

During use of the system, the following identification and authentication procedures may be applied. In general, such identification and authentication procedure may comprise of the steps of medication authentication, complete medication data identification, and single pill identification. As is shown in FIG. 4, when the medication pills are distributed in a blister package in a box, for a first identification and authentication, the following steps are preferably performed by an end user, in accordance with the information provided in FIG. 1. Upon opening a new medication box, the end-user may perform the two steps noted above, including authenticating the L1 Pill layer and the L2 Box Layer (or as noted above, an otherwise electronically or printed version of a code made available to the user, such as transmitted by email, or printed on a prescription label, for example). In order to perform these authentications, preferably an image taken by the user using a webcam or other imaging device of a pill fractal at step 412 (preferably including L1 Pill Layer information 110, basic medication data 120 and L1-L2 key 130) and a box fractal at step 414 (preferably including L2—Box Layer information 140, complete medication data 150 and one-time code 160). These two images are then preferably uploaded to an identification and authentication processor or computer at step 416. This processor may be located locally or may be a remote data processing system located in a remote location, or may be provided in a cloud computing environment. In accordance with embodiments of the present invention, and as described in reference to FIG. 1, the L1-L2 key 130 from the pill fractal image at step 412 may be used to decode information from the packaging fractal obtained at step 414, and both may preferably be employed to properly authenticate and identify the medication pills. Pending successful authentication, an authentication approval and complete medication data will be returned at step 418. During subsequent use of the pills by the end user, these pills previously removed from an authenticated box may be submitted to single pill identification only. The pill fractal may be imaged at step 412 and uploaded to the identification and authentication computer (step 416). The basic medication data (medication name and dosage strength) may be returned (step 418), or the complete medication data may be returned, to prevent erroneous medication consumption.

In U.S. patent application Ser. No. 12/620,686, filed Nov. 18, 2009, titled Method and Apparatus for Verification of Medication Administration Adherence; U.S. patent application Ser. No. 12/646,383, filed Dec. 23, 2009, titled Method and Apparatus for Verification of Clinical Trial Adherence; U.S. patent application Ser. No. 12/646,603, filed Dec. 23, 2009, titled Method and Apparatus for Management of Clinical Trials; and U.S. patent application Ser. No. 12/728,721, filed Mar. 22, 2010, titled Apparatus and Method for Collection of Protocol Adherence Data, the contents of these four applications being incorporated herein by reference, the inventors of the present invention have proposed a system, method and apparatus that allow for complete control and verification of adherence to a prescribed medication protocol or machine or apparatus use in a clinical trial setting, whether in a health care provider's care, or when self administered in a homecare situation by a patient. These applications present the only medication management system that may determine whether a user is actually following a protocol, provide additional assistance to a user, starting with instructions, video instructions, and the like, and moving up to contact from a medication administrator if it is determined that the user would need such assistance in any medical adherence situation, including clinical trial settings, home care settings, healthcare administration locations, such as nursing homes, clinics, hospitals and the like, and in clinical trial settings. It is contemplated in accordance with one or more embodiments of the invention that the system depicted in one or more of these application be used in conjunction with the present invention to provide a further robust identification and authentication system for pill or other medication.

Figure 5:
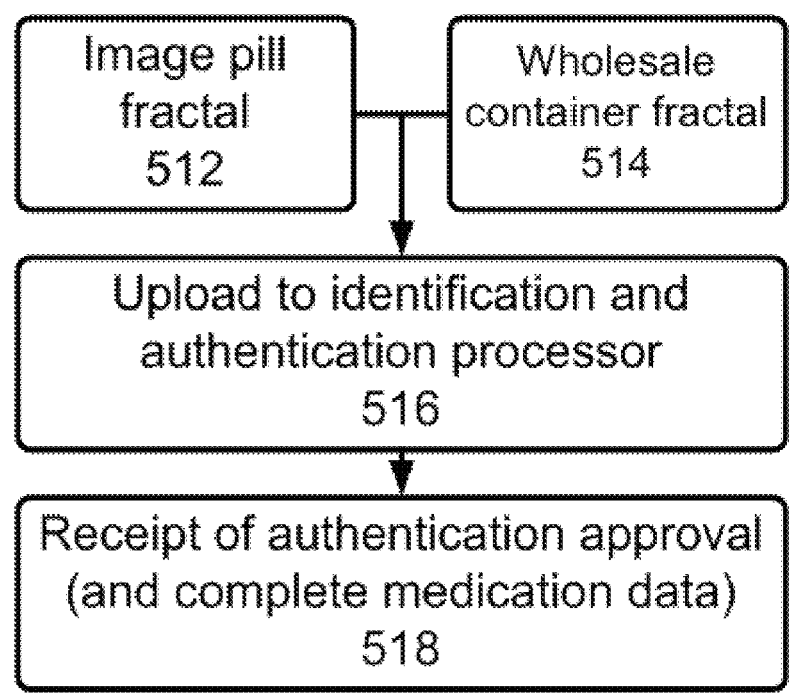
FIG. 5 is a depicts a medication authentication sequence in accordance with an alternative embodiment of the invention.

In an alternative embodiment of the invention, when the medication pills are distributed loosely in a container at both the wholesale and retail levels, as noted above, authentication and identification may be performed at the pharmacy or other distribution center, while subsequent identification may be performed by the end user. As is therefore shown in FIG. 5, upon opening a new wholesale-container, the pharmacist will preferably perform two steps, including a pill layer authentication and a wholesale container layer. To perform these steps, a pill fractal image may be imaged at step 512 and the wholesale container fractal image may be imaged at step 514. At step 516, these two images may be uploaded to an identification and authentication computer, being processed similarly as noted above. Pending successful authentication, an authentication approval and complete medication data may be returned at step 518. Once the end user receives the medication in a retail medication container, since the medication authentication has been performed at the pharmacy, the end-user preferably performs only medication identification. When first using the medication, the end user will preferably, upon opening a new medication retail-container, perform two steps including a pill layer and a retail container layer authentication (in the manner as previously described in FIG. 4). A pill fractal image at step 412 and a retail-container fractal may be image at step 414 may be imaged by the end user and uploaded to an identification and authentication computer at step 416. The complete medication data will be returned upon processing of the fractal images at step 418. Pills subsequently removed from the retail-container (after the initial identification and authentication process) will be submitted to a single pill layer identification only. The pill fractal may be imaged by the end user ate step 412 and uploaded to the identification and authentication computer at step 416. The basic medication data (medication name and dosage strength), or complete medication information will be returned upon proper processing at step 418, to prevent erroneous medication consumption.

For blister-pack and a box packaged medication, an alternative computer assisted medication authentication method is provided in accordance with an alternative embodiment of the invention. As part of the medication purchasing process, a pharmacy's computer may send to the end-user's computer, mobile device, or other computing device, including one or more cloud computing locations, a one-time code needed for medication authentication. Upon opening a new medication box, the end-user may then need to perform one step only of imaging a pill fractal image and uploaded to an identification and authentication computer, The L1-L2 code (described above) may be used to read the one-time code previously sent to the user. Pending successful authentication, and authentication approval, and complete medication data will be returned.

It is contemplated in accordance with one or more embodiments of the invention that the pill fractal may contain relatively little information. Thus, implementation may be performed implementing a fractal like the Cantor square, in a manner as will be described below. It is possible to use a separate fractal for each data field; one for the basic medication data, and one for the L1-L2 code. The packaging (box or wholesale container) fractal preferably may contain a strong one-time code. Such a more complex fractal image may use orbital fractals or L-system fractal curves in a manner as described above. The starting location needed for decoding may preferably be provided by the L1-L2 code on the pill fractal in this situation. Of course, any type of these noted fractal images may be used in any desired case or step. Furthermore, any image including fractal-like qualities may be employed, and thus the invention shall not be considered limited to the use of a true fractal. Thus, any image that is appropriate, and provides one or more desirable fractal qualities may be employed.

Any number of different printing technologies may be employed in order to print a desired fractal or other image on a medication pill or medication container. Such printing technologies may include the following.

Pad Printing

Pad printing is an indirect way of printing. The pad takes up the image from an etched printing plate and transfers it onto the object. By using extremely elastic pads, concave, convex, regular and irregular shaped objects can be printed. Pad printing can transfer a 2D image onto a 3D object. This is accomplished using an indirect offset printing process that involves an image being transferred from the cliché via a silicone pad onto a substrate. Pad printing is used for printing on otherwise impossible products in many industries including medical, automotive, promotional, apparel, and electronic objects, as well as appliances, sports equipment and toys. It can also be used to deposit functional materials such as conductive inks, adhesives, dyes and lubricants. Physical changes within the ink film both on the cliché and on the pad allow it to leave the etched image area in favor of adhering to the pad, and to subsequently release from the pad in favor of adhering to the substrate. The unique properties of the silicone pad enable it to pick the image up from a flat plane and transfer it to a variety of surfaces, such as flat, cylindrical, spherical, compound angles, textures, concave, or convex surfaces.

Image plates are used to contain the desired artwork image etched in its surface. Their function is to hold ink in this etched cavity, allowing the pad to pick up this ink as a film in the shape of the artwork, which is then transferred to the substrate. There are two main types of printing plate materials: photopolymer and steel. Photopolymer plates are the most popular, as they are easy to use. These are typically used in short to medium production runs. Steel plates come in two forms: thin steel for medium to long runs, and thick steel for very long runs. Both steel plate types are generally processed by the plate supplier as it involves the use of specialized equipment.

Pads are three dimensional objects typically molded of silicone rubber. They function as a transfer vehicle, picking up ink from the printing plate, and transferring it to the part (substrate). They vary in shape and diameter depending on the application. There are two main shape groups: round pads and long narrow pads called bar pads. Pads are also made in other shapes, called loaf pads. Within each group there are three size categories: small, medium, and large size pads. It is also possible to engineer custom-shaped pads to meet special application requirements.

Pad printing inks are solvent-based and require mixing with additives before use. They typically seem dry to the touch within seconds although complete drying (cure) might take a substantially longer period of time. There are many more options. Inks that cure via the use of Ultra Violet light are convenient for certain applications. Also there are heat curable inks, which work in much the same way as UV in the sense that there is a trigger that cures the ink when pulled. Two part inks usually have a pot life of only a few hours or so.

Substrate is the technical term used to address any parts or materials to be printed. Fixtures vary in materials and complexity depending on the application. Substrates need to be clean and free from surface contamination to allow proper ink adhesion.

Pad printing technology is often used to print information to a medication pill in high resolution pill printing machines. This type of pill printer utilizes a soft, FDA approved, silicone pad to transfer the images from a flat etched plate to the pill. The image is transferred to the pill while the tablet is preferably held in place by a vacuum plenum. While being sent through the printing process, the pills are held in series of segment plates, with cavities made specifically for the particular pill being printed. These printing machines can print on a wide range of tablet sizes and shapes, such as on oval, round, and oblong with a printing capacity of up to 400,000 pills per hour, and printing resolution of 0.1 mm.

Laser Marking

Laser marking, is the practice of using lasers to engrave or mark an object. The technique does not involve the use of inks, nor does it involve tool bits which contact the engraving surface and wear out. These properties distinguish laser engraving from alternative engraving or marking technologies where inks or bit heads have to be replaced regularly.

Product laser marking is one of the most common industrial applications of lasers. The laser marking systems using different lasers and optical delivery systems may be used to mark an almost endless list of materials including metals, plastics, ceramics, glass, wood and leather as well as painted surfaces and photographic emulsions.

There are two basic methods for laser marking: they are mask marking and beam deflected marking. Both methods take advantage of the relatively high powers generated by lasers. Both methods also use optical techniques to enhance the power densities to levels sufficient to etch the surface of the material to be marked.

In mask marking, a stencil of the desired mark is projected onto the work-piece. The picture of the mask on the object is made using a lens. An extremely short impulse of light energy is directed on the work-piece. Therefore, employed in the mask marking are often the pulsed lasers such as pulsed TEA $CO_2$ laser, excimer laser, and pulsed Nd:YAG laser.

In the beam deflected method, the laser is directed via two galvanometer mirrors and a lens system to the object to be marked. Using special software, a computer controls the galvanometer mirrors. The marking is made by directing the beam in directions x and y. The beam deflection method is very flexible and can transmit a high density of information. The lasers used in this method are often CW $CO_2$ laser and CW Nd:YAG laser.

The marking processes include one or a combination of the following processes:
 a) Bleaching or changing the color of a colorant in the material,
 b) Physical modification of the surface finish,
 c) Scribing a shallow groove into the material by vaporisation,
 d) Highly-controlled modification of the surface by melting.

Laser marking is superior in quality and flexibility to traditional marking techniques. It is suitable for automation and integrated production techniques. The common advantages of all laser marking techniques are:

a) Permanent, high quality marks,
 b) High efficiency and low operation cost,
 c) Good accessibility, even to irregular surface,
 d) Non-contact marking and no special working environmental needed,
 e) Easy to automate and integrate (direct writing of patterns can established using computer-controlled movement of the beam or sample),
 f) Precise beam positioning and a beam highly localised energy transfer to the work-piece,
 g) High reproducibility, high speed and throughput, and
 h) Contamination-free.

An on-tablet marking technique for the pharmaceutical and nutritional industries has been developed. Indeed, companies are available to aid in the design and technical support of advanced coating systems for pharmaceutical and nutritional supplement dosage forms, and to provide assistance in the development of solid dosage formulations. Such a process provides an edible, on-tablet marking technique for recording information such as product identification numbers and markings (human-readable barcodes), unique product logos, patient details, dosage information, and 'use by' dates directly on a tablet. Tablets may be numerically serialized readily in one production campaign with no two tablets being identical. Use of such printing with the images of the present invention will help to eliminate medication errors and counterfeiting, and increase the traceability of drugs. Additives in material in such a medication pill or in a film coating induces a color change in the film coating precisely at locations on the tablet surface exposed to a low-power, $CO_2$ laser.

Edible Stickers

Either of these printing techniques may also be applied to an edible sticker or the like, allowing for the printing of these stickers, and then application of the stickers to the medication pills at a later time. To achieve the required complexity and iterations depth, very high printing resolution shall be needed. A possible approach can be printing the pill fractals on stickers, using a very high (sub-µm) resolution laser lithography. The stickers may be printed in an off-line process, and then stamped onto the pills as part of the production line.

Any of these printing techniques, or other techniques giving similar resolutions, or better, may be employed in accordance with one or more embodiments of the invention. Thus, based upon a level of desired resolution of one or more printed fractal images, one or more of these printing technologies may be identified as appropriate.

Fractal Systems Library

One or more fractal systems libraries for use with the pill authentication and identification scheme will now be described. In accordance with the various embodiments of the present invention several inventive mathematical methods are described to create fractal images at various complexity levels and emphasize their applicability for identification purposes. In addition, various methods are outlined on how to recover the included codes from the fractal images. Moreover, procedures for including one or more keys necessary for the parameter recovering process are also provided. These inventive methods are based on the mathematical theory of dynamical systems, iterated function systems and symbolic systems. Libraries of images having one or more desirable fractal characteristics may also be employed, and therefore this invention should be considered applicable to fractal-like images in addition to true fractal images.

Dynamical Systems Method

General Description—

In accordance with an embodiment of the invention, one may use a discrete time dynamical system given by a map f:

M→M to generate one or more of the inventive fractal patterns. Here M is a subset of $R^k$, the k-dimensional Euclidean space. While taking iterations $f^n$ of f and applying $f^n$ to points x in M the orbit of x by the formula is obtained $$O^+(x)=\{f^n(x):n=0,1,2,\ldots\}.$$

The orbit describes the time evolution of the state x at time n. For details about the general theory of dynamical systems reference is made to the books by Katok and Hasselblatt (A. Katok and B. Hasselblatt, Introduction to the modern theory of dynamical systems. Encyclopedia of Mathematics and its Applications, 54, Cambridge University Press, Cambridge, 1995) and Robinson (C. Robinson, An Introduction to Dynamical Systems, 2nd Edition, American Mathematical Society, Pure and Applied Undergraduate Texts, 2012). For large classes of dynamical systems there exists an invariant set $J \subset M$ that carries the complexity of the dynamical system. Here invariant refers to the condition $J=f^{-1}(J)=f(J)$ and the notion of complexity is meant in various ways such as full topological or metric entropy, determining the asymptotic dynamical behavior of every (almost every) orbit, positive Lyapunov exponents, maximal fractal dimension, etc. One may consider dynamical systems f for which the corresponding invariant set J is a fractal set.

For identification purposes, in accordance with an embodiment of the present invention, one may preferably apply an inventive method that can be outlined as follows: Rather than considering one single dynamical systems f one may consider a family of dynamical systems $f_c$ (within a particular class of systems) and consider the associated invariant sets $J_c$ (i.e. the fractals). Here c is a parameter in a large set (in most applications a subset of l-dimensional real or complex Euclidean space). The identification method in the context of pills in accordance with an embodiment of the invention may work as follows. In step 1 a parameter c may be selected in the parameter space and use methods from dynamical systems to obtain an image of the fractal set $J_c$. Next one may print this image on the pill. In a second step the pill is preferably scanned (imaged) and the obtained image is used to recover the parameter c and therefore to identify the pill. The mathematical procedures in step 2 (recovery of the parameter c) are highly complex and this complexity may be applied in a way that the recovery requires additional information about the fractal images. This information is preferably used as a key that is necessary to correctly identify the parameter c. In the following several concrete classes of dynamical systems $f_c$ are described and explain how to obtain the corresponding fractal sets $J_c$.

One-Dimensional Complex Dynamics and Julia Sets—In one-dimensional dynamics one considers the dynamics of complex polynomials (and more generally the dynamics of rational maps on the Riemann sphere) and studies the relevant invariant sets that exhibit certain kind of dynamical behavior. For simplicity only polynomials will be presently considered, but many of the concepts generalize to rational maps. The books by Milnor (Milnor, Dynamics in One Complex Variable, third edition, 2006) and Carleson and Gamelin (L. Carleson and T. Gamelin, Complex dynamics, Springer, New York, 1993) provide reference information on the subject.

Consider a positive integer d and complex numbers $c_0, \ldots, c_d$. A complex polynomial $f: \mathbb{C} \to \mathbb{C}$ is given by the formula $$f(z)=c_d z^d+c_{d-1}z^{d-1}+\ldots+c_0.$$

Figure 6:
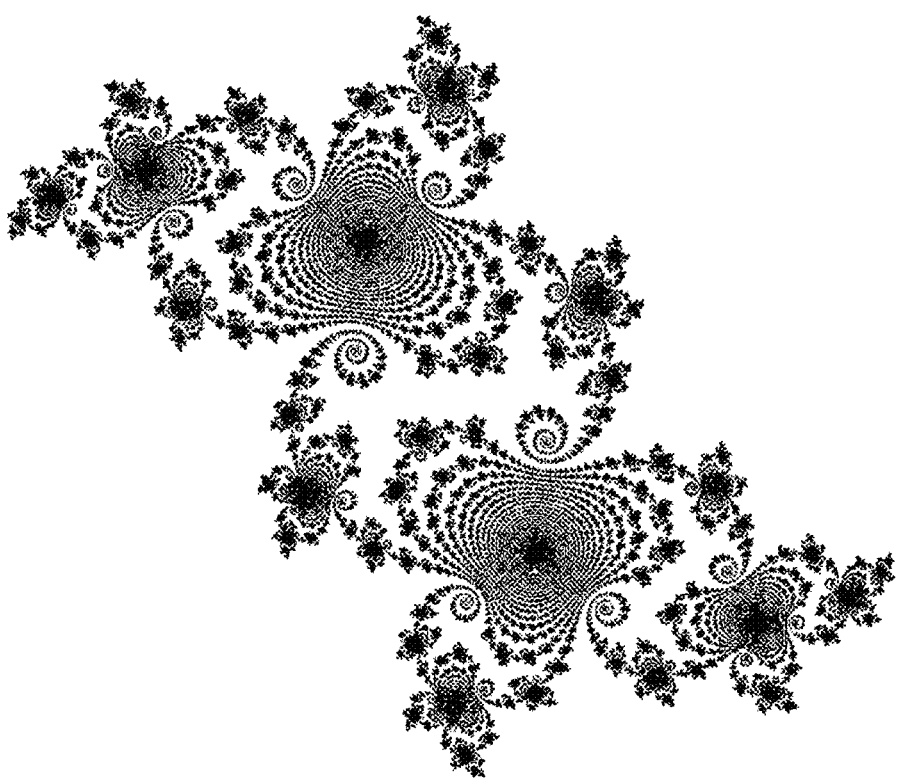
FIG. 6 depicts the result of an image generated in accordance with a Julia set of a predetermined quadratic polynomial in accordance with an embodiment of the invention.

One may frequently write $f=f_c$, where $c=(c_0, \ldots, c_d)$ to indicate the dependence of the polynomial f on the parameter c. The set of points in the complex plane with complicated dynamics is called the Julia set $J=J_c$. One way to define the Julia set is that it coincides with the topological boundary of the set of points with bounded forward orbit (i.e. the so-called filled-in Julia set). The Julia sets are in general highly complex fractals (see for example FIG. 6); Further different parameters c lead to different Julia sets. FIG. 6 depicts the Julia set of the quadratic polynomial $z \mapsto z^2-0.1+0.65i$.

One may use the parameter c to store the relevant information. The Julia set can be computed via the following iteration algorithm.

Step 1. Pick a parameter c, assign to it the polynomial $f_c$, compute an image of the fractal set $J_c$ and print this image on the object to be identified (for example a pill). Next, the image of the Julia set $J_c$ is preferably scanned and one may apply mathematical methods to recover the parameter c and use c to identify the information stored on the pill. In particular, one may use numerical methods based on Hausdorff metric and Hausdorrff semi-metric computation to identify (recover) the parameter c.

Step 2. Scan the image on the fractal $J_c$ and apply algorithms to recover the parameter c.

In the general, the different types of complexity in the Julia sets are so rich that the computations necessary to recover the parameter c may be rather costly. In that case one may preferably restrict the range of allowable parameters to regions where the identification procedure can be carried out sufficiently effective. Alternatively, one may use this complexity to add another component to the procedure namely the requirement of a key to compute the parameter c.

For this, one may preferably identify certain regions $R_1, \ldots, R_l$ in the parameter space all of which are close to the bifurcation locus of the dynamics of the polynomials $f_c$. Here 1 is a rather large positive integer. In the case d=2 the bifurcation locus is the boundary of the well-known Mandelbrot set and in the case d>2 one may use its natural generalizations (i.e. the boundaries of the Multibrot sets). One may compute these sets using algorithms based on the asymptotic behavior of the orbits of the critical points of the polynomial. The key for the analysis is now the specific parameter region $R_i$. For simple applications it can be encoded numerically and for more complex applications it can be encoded in a fractal image of the region of the bifurcation locus.

Step 2b (with key encryption). First identify the region $R_i$ either numerically or via fractal identification. Next use the fractal identification procedure (see Step 2) to recover the identifying parameter $c \in R_i$.

Dynamics of Complex Henon Maps—Complex Henon maps are prototypes of two-dimensional invertible complex dynamical systems with non-trivial dynamics. These maps have been intensively studied during the last two decades including fundamental contributions by Bedford and Smillie (E. Bedford and J. Smillie, Polynomial diffeomorphisms of C2: Currents, equivlibrium measure and hyperbolicity, Invent. Math. 103 (1991), 69-99; E. Bedford and J. Smillie, Polynomial diffeomorphisms of C2 3: Ergodicity, exponents and entropy of the equilibrium measure, Math. Ann. 294 (1992), 395-420) and Fornaess and Sibony (J. E. Fornæss and N. Sibony, Complex Hé non mappings in C2 and Fatou-Bieberbach domains, Duke Math. J. 65 (1992), 345-380). Some of the basic theory of these systems is summarized in the textbook (S. Morosawa, Y. Nishimura, M. Taniguchi and T. Ueda, Holomorphic dynamics, Cambridge Studies in Advanced Mathematics, 2000).

A complex Henon map is a polynomial map $f=f_{a,c}: \mathbb{C}^2 \to \mathbb{C}^2$ defined by $$(z,w) \mapsto (P_c(z)+aw,z),$$

where $P_c$ is a complex polynomial of degree d, $c=(c_0,\ldots,c_d)$ and a is a non-zero complex number. The map f is invertible with polynomial inverse $f^{-1}$. One may define $$K^+=\{(z,w):O^+(z,w) \text{ is bounded}\}$$

and $J^+=\partial K^+$. These sets are referred to as the forward filled-in Julia set (respectively forward Julia set of f). Analogously one may define $K^-$ and $J^-$ for the map $f^{-1}$. The forward/backward Julia sets play the analogous role as the Julia set in one-dimensional dynamics.

Figure 7:
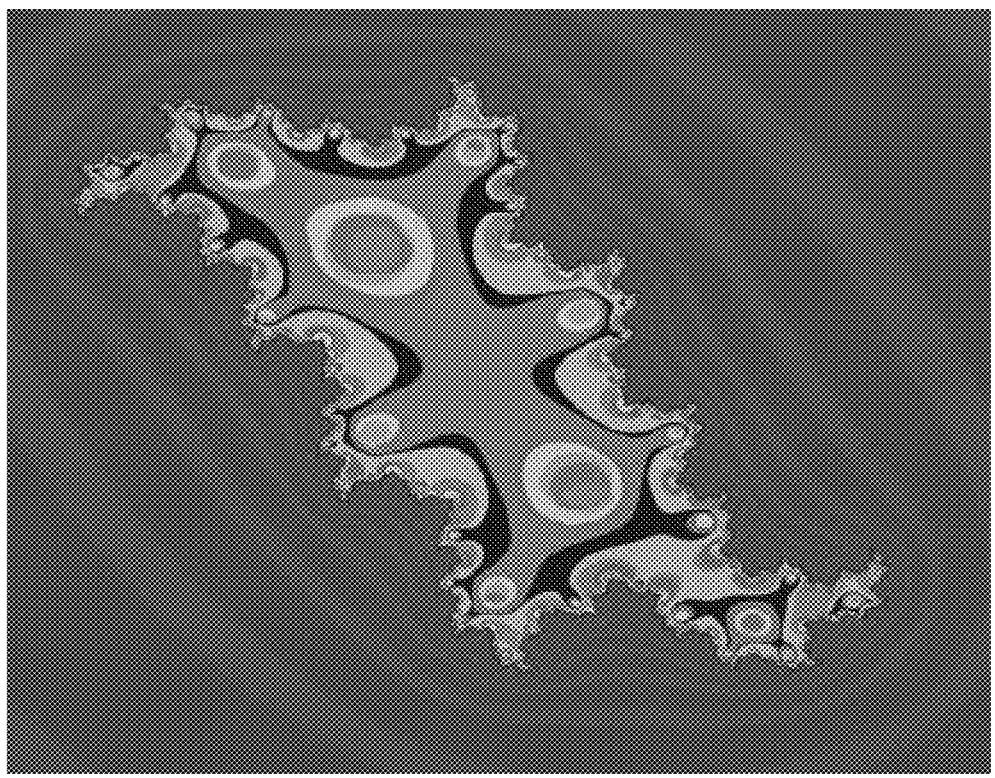
FIG. 7 depicts the result of an image generated in accordance with a Henon map in accordance with an embodiment of the invention.
Figure 8:
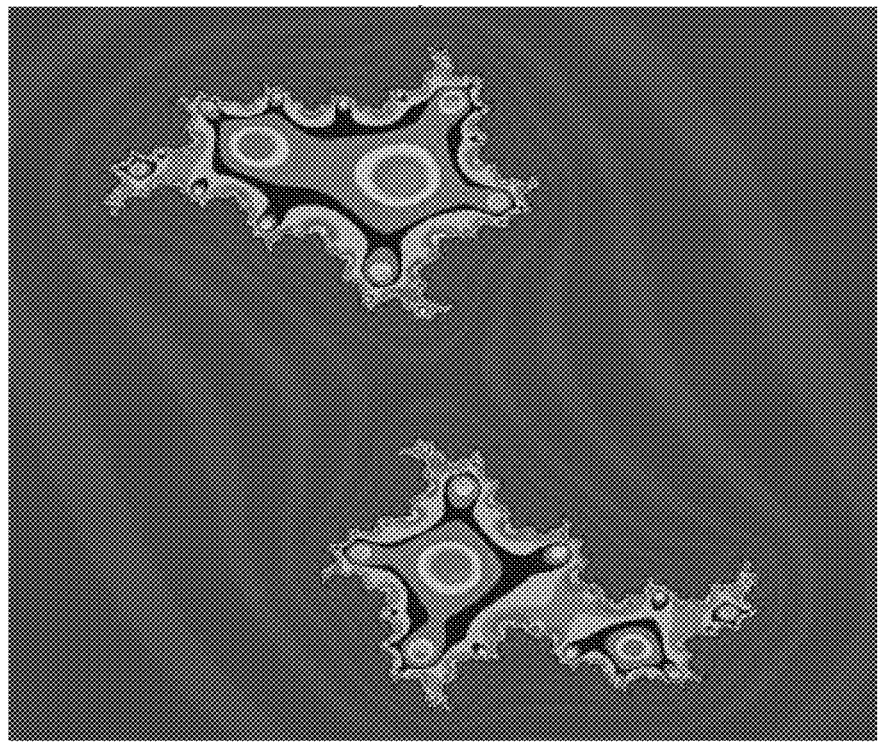
FIG. 8 depicts the results of an image generated in accordance with the Henon map of FIG. 7, but at a different slice value.

One feature of complex Henon maps is that the Green functions of the set $K^+$ have a dynamical characterization. Namely, $$G^+(z,w) = \lim_{n\to\infty} \frac{1}{d^n}\log^+\|f^n(z,w)\|$$

defines the Green function of the set $K^+$ (with the analogous formula for the Green function of $K^-$. One may use the fact that the level sets of the Green functions are smooth hyper surfaces. While the fractal $J^+$ and the level sets of the Green functions are objects in two-dimensional complex space (and therefore are four-dimensional real objects), one may consider slices of these sets with a complex line which results in a one-dimensional complex object. The corresponding complex line L is used as a key that is required to create the fractal image and also to recover the parameter from the printed image. These images have a highly complex structure and different slices lead to different images. For example, in FIG. 7 one may consider the map $f(z,w)=(z^2+0.25+0.5i+0.1w+0.05iw,z)$ and the slice=3i, while one may consider in FIG. 8 the same Henon map f with the slice $w=3$. The boundaries between the different areas are the level sets of the Green function. Note that mathematically the key L is uniquely determined by two complex numbers that serve as an identifier of the key. FIG. 7 depicts the set $J^+$ for the map $(z,w)\mapsto(z^2+0.25+0.5i+0.1w+0.05iw,z)$, and the key $L_1:w=3i$. FIG. 8 depicts the set $J^+$ for the map $(z,w)\mapsto(z^2+0.25+0.5i+0.1w+0.05iw,z)$ and the key $L_2:w=3$.

In particular, one preferred method in accordance with an embodiment of the invention may include a method based on the following procedure:

Step 1. Pick parameters a and c, assign to it the complex Henon map $f_{a,c}$. Pick a key L and compute the image of the fractal set $J_{a,c}^+\cap L$. Include in this image selected level curves of the Green function $G_{a,c}^+$. Print this image on the pill.

Step 2. Scan the image of the fractal on the pill and apply a dynamical based algorithm to recover the parameter (a,c). Note that this step requires knowledge of the key L.

Figure 9:
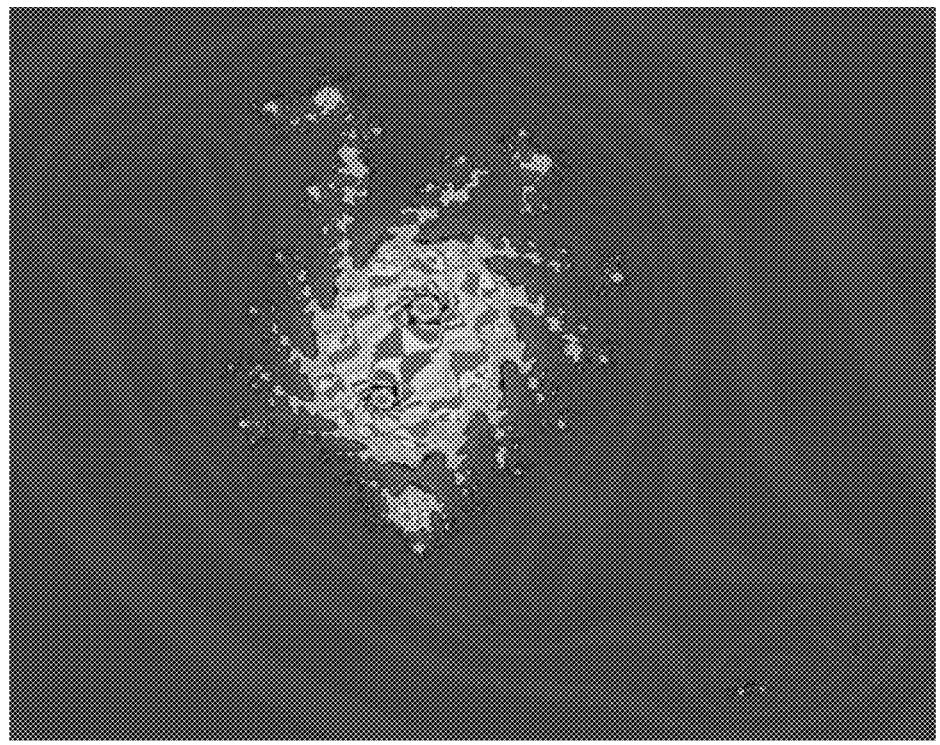
FIG. 9 depicts the results of an image generated in accordance with a further Henon map in accordance with an embodiment of the invention.

To illustrate that different maps correspond to different fractals, FIG. 9 presents the set $J^+$ for the map $f(z,w)=(z^2+0.5+0.25i+0.5w+0.3iw,z)$ and the slice $w=3$, where the key $L_3:w=i$.

Deterministic Fractal Attractors—

Attractors are compact invariant sets that attract points that are nearby. Basic properties of attractors can be found in the book by Robinson (C. Robinson, An Introduction to Dynamical Systems, 2nd Edition, American Mathematical Society, Pure and Applied Undergraduate Texts, 2012). Let f: M→M be a smooth dynamical system where M is a subset of $R^k$, that is the k-dimensional real Euclidean space. One may say a compact (closed and bounded) f-invariant set $\Lambda$ is an attractor if there exists an open set $U\subset M$ containing $\Lambda$ such that each point x in U converges to $\Lambda$ under iteration of f. One may consider parameterized families $f=f_a$, where a is a parameter in a j-dimensional parameter space, that have an attractor $\Lambda_a$. The parameter a is used to identify the information associated with the pill. In accordance with an embodiment of the invention, one may preferably print the image of the attractor (or of a two-dimensional slice in case k>2) on the pill. One may use an iteration method analysis to recover the parameter a. This method works particularly efficiently if $\Lambda_a$ is a hyperbolic attractor in which case the geometric speed of convergence will allow a fast reconstruction of the parameter a.

Quasi-Random Fractal Attractors With Key Requirement—

Here, in accordance with an embodiment of the present invention, one may preferably consider finitely many contracting maps $f_{a_1},\ldots,f_{a_k}:M\to M$ and compose them in a pre-determined order. Here the parameters $a_1,\ldots,a_k$ belong to parameter spaces $R_1,\ldots,R_k$ that are subsets of some Euclidean space. The order how to compose the maps $f_{a_i}$ is given by a key $S=(s_1,s_2,s_3,\ldots)$, where all $s_i\in\{1,\ldots,k\}$. The key S and the parameter $a_1,\ldots,a_k$ determine the fractal set $$\Lambda = \bigcap_{j\in\mathbb{N}} f_{a_{s_j}}\circ\ldots\circ f_{a_{s_1}}(M).$$

On the other hand, using the key S one may apply the Hausdorff metric or Hausdorff semi-metric based iterative parameter search algorithm to reconstruct the parameter $a_1,\ldots,a_k$. The resulting method is illustrated by the following two steps.

Step 1. Pick parameters $a_1,\ldots,a_k$, assign to it the contracting maps $f_{a_1},\ldots,f_{a_k}:M\to M$. Pick a key S and compute an image of the fractal set A. Print this image on the pill.

Step 2. Scan the image of the fractal on the pill and apply an iterative parameter search algorithm to recover the parameters $a_1,\ldots,a_k$. Note that this step requires knowledge of the key S that can be transmitted in several ways.

Permutation Sub-Groups

General Description—

In theory, every data set can be encoded by a finite set of numbers. For simplicity, in accordance with a preferred embodiment of the invention one may use positive integers to code the necessary information on the pill. Therefore, the set of all possible codes can be modeled by a set $C=\{1,\ldots,n\}$, where n is a rather large positive integer. In this context a key is a one-to-one and onto map from C to C. Such a map is called a permutation. One may preferably denote the set of all possible permutations as Per(n). The set Per(n) together with composition of maps carries the mathematical structure of a group with n! elements. Every finite set of permutations $p_1,\ldots,p_k$ generates a subgroup $G_{p_1,\ldots,p_k}$ of Per(n) that is determined by $p_1,\ldots,p_k$. One may call $p_1,\ldots,p_k$ the generators of the subgroup $G_{p_1,\ldots,p_k}$. Once the generators are fixed every key $S=(i_1,\ldots,i_l)$ uniquely determines an element $p\in G_{p_1,\ldots,p_k}$ via the formula $$p=p_{i_l}\circ\ldots\circ p_{i_1}$$

In accordance with one or more embodiments of the present invention, one may apply the theory above to code several subclasses of pills (by company, pill type, chemical family, etc.) and assign to each of these subclasses of pills a well-defined subgroup $G=G_{p_1,\ldots,p_k}$. A specific key S may then be defined that is used to encrypt images to be applied to the pills associated with the subgroup G.

Iterated Function Systems

General description—A natural way to construct fractal images is given by a so-called iterated function system (IFS). This construction following Falconer [F]. Let $M\subset R^k$ be a compact set and let $T_1, \ldots, T_k:M \to M$ be contractions (i.e. Lipschitz continuous functions with Lipschitz constants strictly smaller than one). Then there exists a unique compact set J with the property $$J = \cup_{i=1}^{k} T_i(J).$$

In other words J is the unique fixed point of the transformation $X \mapsto T(X) = \cup_{i=1}^{k} T_i(X)$ acting on the space of all compact non-empty subsets of M. Moreover, for all such X the sequence $X, T(X), T^2(X), T^3(X), \ldots$ converges to the fixed point J (with respect to the Hausdorff metric) at a geometric rate of convergence. The fractal J is then preferably printed on a pill and, after scanning the image, may be used to calculate the parameter determining the maps $T_i$. These parameters identify the information associated with the pill. A particular application of this technique is the construction of so-called Cantor squares and is described in the following section.

Cantor Code— the above-noted Cantor square fractal images will now be described. In accordance with the various embodiments of the invention, a method to encode information in a 2-dimensional image (similar to a barcode or QR code) and a method to scan the image and recover that information are provided. The encoding method preferably utilizes a variant of Cantor products (2-dimensional fractal patterns based on Cantor sets), while the scanning method is derived from Hausdorff-based image matching techniques, and utilizes the fractal nature of Cantor products.

Cantor Sets—

The middle-third Cantor set is one of the most well-known fractals. It is constructed through an iterative process: starting with the unit interval $E_0 = [0,1]$, the middle-third interval $$\left(\frac{1}{3}, \frac{2}{3}\right)$$

is removed so that $$E_1 = \left[0, \frac{1}{3}\right] \cup \left[\frac{2}{3}, 1\right].$$

At the next iteration, the middle-thirds of these intervals are removed so that $$E_2 = \left[0, \frac{1}{9}\right] \cup \left[\frac{2}{9}, \frac{1}{3}\right] \cup \left[\frac{2}{3}, \frac{7}{9}\right] \cup \left[\frac{8}{9}, 1\right].$$

Figure 10:
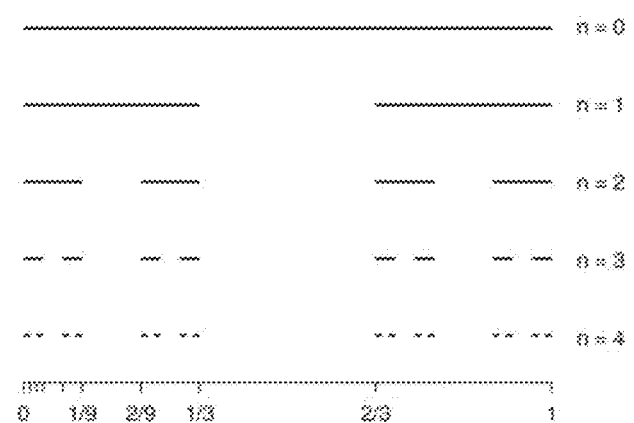
FIG. 10 is a depiction of the first four iterations of the middle-third Cantor set.

This process is continued so that $E_n$ is constructed by removing the middle-thirds of each interval in $E_{n-1}$. FIG. 10 illustrates this process for the first four iterations, depicting four iterations of the middle third Cantor set.

This construction process may be generalized by changing the length of the starting interval, increasing/decreasing the fraction of the interval that is removed, adjusting the location of the interval that is removed, changing the sizes of all line segments at each iteration, etc. In this paper, the term Cantor sets will refer to 1-dimensional fractals generated by this generalized construction process.

Cantor Products—

Figure 11:
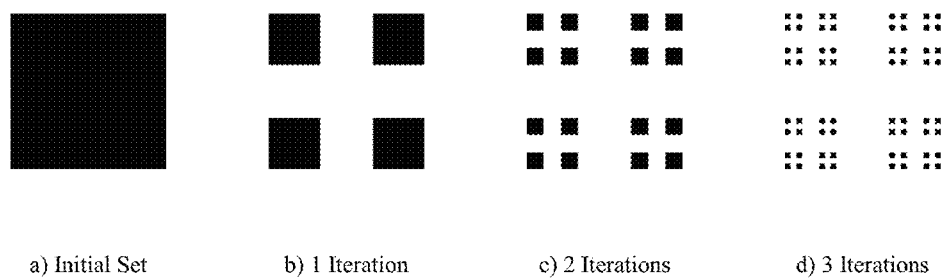
FIG. 11 is a depiction of the first three iterations of a Cantor product.

Cantor products are 2-dimensional fractals generated by taking the Cartesian product of two Cantor sets. The most commonly seen example is known as Cantor dust and is the Cartesian product of two middle-third Cantor sets. An example can be seen in FIG. 11.

Figure 12:
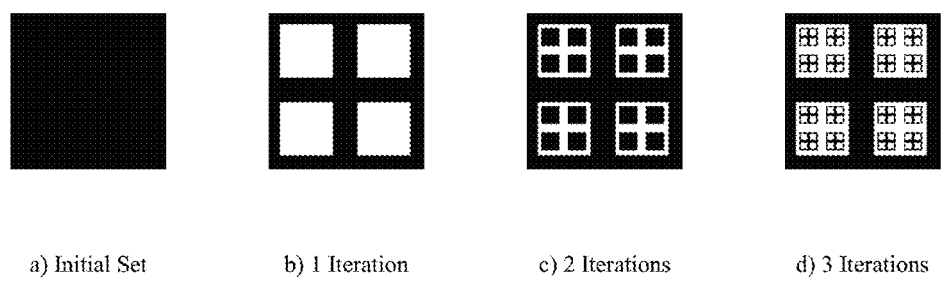
FIG. 12 is a modified version of the Cantor product of FIG. 11 in accordance with an embodiment of the invention.

The inventors of the present invention have determined that a variant of Cantor products can be generated by taking the Cartesian product of two generalized Cantor sets and then layering successive iterations on top of each other, preferably in alternating colors, or the like. Other types of fractal combinations or bases can be employed, and the invention should not be considered so limited tone type of fractal image. Various relative positioning between the overlaid images to provide further information and provide different visual patterns of the information. The resulting image is not necessarily a true fractal, but is useful for keeping track of the changes at each iteration. This construction is demonstrated in FIG. 12. In FIG. 12, each iteration is placed on top of the previous iteration, preferably in different or alternating colors. During each iteration, the construction process preferably involves not only removal of an interval each dimension, but also scaling and translation of all intervals.

As is shown in FIG. 12, each iteration is preferably placed on top of the previous iteration, in alternating colors. Notice that at each iteration, the construction process involves not only removal of an interval in each dimension, but also scaling and translation of all intervals.

Cantor Generation—

Generation of these inventive alternative cantor product construction will now be described. An affine transformation is defined as a transformation of the form $$A(x, y) = \begin{pmatrix} a & b \\ c & d \end{pmatrix} \begin{pmatrix} x \\ y \end{pmatrix} + \begin{pmatrix} e \\ f \end{pmatrix} = (a \cdot x + b \cdot y + e, c \cdot x + d \cdot y + f).$$

If $\det(A) = |ad - bc| < 1$, then A is called a contraction mapping, i.e., A brings points closer together. Affine transformations involving only scaling and translation have the form $$A(x, y) = \begin{pmatrix} a & 0 \\ 0 & d \end{pmatrix} \begin{pmatrix} x \\ y \end{pmatrix} + \begin{pmatrix} e \\ f \end{pmatrix} = (a \cdot x + e, d \cdot y + f).$$

In this form, a and d represent scaling factors in the x- and y-directions, while e and f represent translations in the x- and y-directions. If a and d are both less than 1, than A is clearly a contraction mapping.

The space of contraction mappings involving only scaling and translation is clearly a subset of the space of affine translations. In this application, T will denote this space, and the word transformation will refer to these specific mappings. The proposed 2-dimensional Cantor codes are preferably generated using the alternative construction from FIG. 12. The Cantor codes can be defined as an Iterated Function System (IFS), where the nth iteration is generated by applying four transformations $\tau_i$, i=0, 1, 2, 3, to the n−1 iteration, switching the colors, and placing the nth iteration on top of the n−1 iteration. In this application, the convention is for $\tau_0$ to map the n−1 iteration to the upper-left quadrant of the nth iteration, $\tau_1$ to the upper-right quadrant, $\tau_2$ to the lower-right quadrant, and $\tau_3$ to the lower-left quadrant. This ordering arises from the fact that images are represented on a computer as a matrix I of pixel-intensity values; hence I[0,0] corresponds to the pixel in the upper-left corner of the image. As a result, the positive x-direction is top to bottom, the positive y-direction is left to right, and the quadrants are ordered in a counter-clockwise orientation.

Each transformation has the form $$\tau(x, y) = \begin{pmatrix} s_x & 0 \\ 0 & s_y \end{pmatrix} \begin{pmatrix} x \\ y \end{pmatrix} + \begin{pmatrix} t_x \\ t_y \end{pmatrix} = (s_x \cdot x + t_x, s_y \cdot y + t_y),$$

with $\det(\tau)=|s_x \cdot s_y|<1$, and where $s_x$ is the scaling factor in the x-direction, $s_y$ is the scaling factor in the y-direction, $t_x$ is the translation in the x-direction, and $t_y$ is the translation in the y-direction. The transformations can be conveniently represented in vector form as $$\tau=[s_x,s_y,t_x,t_y],$$

with each entry written as a percentage. A 2-dimensional Cantor code can then be encoded as a 4×4 matrix T with the ith row representing the ith transformation. For an image I of m×n pixels (m is the number of rows and n the number of columns), $\tau$ would map I to a smaller version of itself that would be of size $s_x \cdot m \times s_y \cdot n$. It would be translated vertically by $t_x \cdot m$ pixels and translated horizontally by $t_y \cdot n$ pixels. To preserve the open set condition, $s_x+t_x<0.5$ and $s_y+t_y<0.5$. (The transformations $\tau_i$ satisfy the open set condition if for an open set O, the transformations are contraction mappings that satisfy the following two conditions: $\cup_{i=1}^n \tau_i(O) \subset O$ and $\tau_i(O) \cap \tau_j(O)=\text{Å}$ if $i \neq j$. The open set condition ensures minimal overlap when taking a union of contraction mappings).

FIG. 12 is generated by the matrix $$T = \begin{pmatrix} 0.34 & 0.34 & 0.07 & 0.07 \\ 0.34 & 034 & 0.07 & 0.07 \\ 0.34 & 0.34 & 0.07 & 0.07 \\ 0.34 & 0.34 & 0.07 & 0.07 \end{pmatrix}$$

Figure 13:
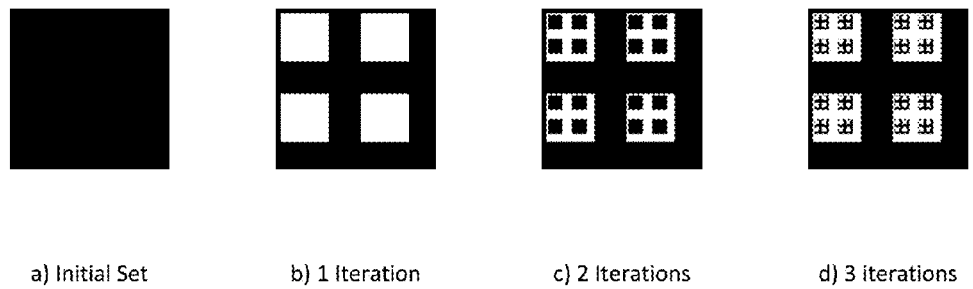
FIG. 13 is a further modified version of the modified Cantor product of FIG. 12 in accordance with an embodiment of the invention.

FIG. 13 is generated by the matrix $$T = \begin{pmatrix} 0.30 & 0.30 & 0.03 & 0.03 \\ 0.30 & 0.30 & 0.03 & 0.03 \\ 0.30 & 0.30 & 0.03 & 0.03 \\ 0.30 & 0.30 & 0.03 & 0.03 \end{pmatrix}$$

Figure 14:
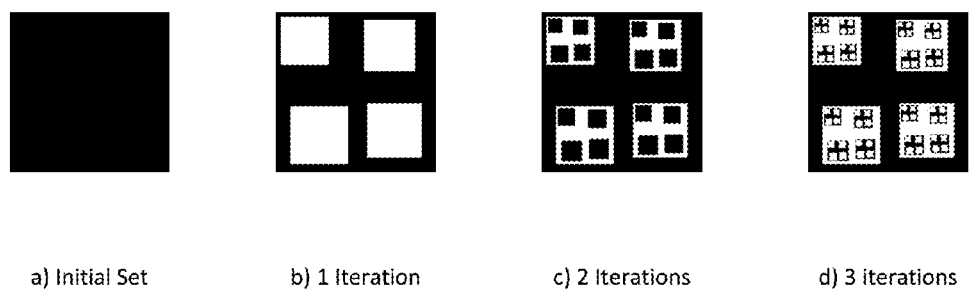
FIG. 14 is a still further modified version of the modified Cantor product of FIG. 12 in accordance with an embodiment of the invention.

FIG. 14 is generated by the matrix $$T = \begin{pmatrix} 0.30 & 0.30 & 0.03 & 0.03 \\ 0.32 & 0.32 & 0.05 & 0.05 \\ 0.34 & 0.34 & 0.07 & 0.07 \\ 0.36 & 0.36 & 0.09 & 0.09 \end{pmatrix}$$

Scanning Method

Once generated and positioned on an object, such as a medication pill or the like, recovery of the matrix T from an image of a Cantor code is preferably based on Hausdorff distance-based image matching in accordance with an embodiment of the invention. In computer vision, image matching is the following problem: given a model M and an image I, find M in I. If M exists in I, then there exists an affine transformation A that, when applied to M, moves A(M) into the correct location in I at the correct size and orientation. The similarity between A(M) and some subset of I is checked using the Hausdorff distance, which measures the similarity between two sets of points.

The scanning method for Cantor codes uses the entire Cantor code as the model M and the 4 quadrants of the Cantor code as the images Ii, i=0, 1, 2, 3, to recover the transformations $\tau_i$, i=0, 1, 2, 3. This method takes advantage of the fractal nature of the Cantor codes by searching for a transformed version of the Cantor code inside itself, i.e., the Cantor code supplies both M and I.

The problem of finding the correct contraction mappings may be solved using brute-force, but quickly runs into combinatorial issues. For example, if each of the 16 parameters in T can take just 5 possible values, then the number of contraction mappings to search through is $5^{16}=152,587,890,625$. Since the space of affine transformations is so large, efficient search techniques must be used. In addition, computing the Hausdorff distance requires computing nearest-neighbor distances between every point in one set to every point in the other set. For large point sets, this can be computationally expensive. An alternative method of computing nearest-neighbor distances may be preferably used.

Image matching involves comparing an image I and a transformed model A(M) and determining if they are "close" to each other. The scanning method for Cantor codes uses image matching techniques that are based on the Hausdorff distance to compute the distance between I and $\tau$(M) for some $\tau \in T$. Intuitively, the Hausdorff distance between I and M is small if every point of I is close to a point of M and every point of M is close to a point of I. This concept may be used to determine how much I and M look alike.

Ideally, it would be preferable if the Hausdorff distance were a metric (although any function that allows for image matching may be employed to measure similarities of any repetitive formations at multiple iteration levels), that is, the Hausdorff distance is a function $d: I \times M \rightarrow \mathbb{R}$ with the following properties:
1) $d(I,M) \geq 0$
2) $d(I,M)=0$ if and only if $I=M$
3) $d(I,M)=d(M,I)$
4) $d(I,M) \leq d(I,X)+d(X,M)$ One would also want d to be positive. Intuitively, line 2 above states that an image should only be identical to itself, line 3 states that the order of comparison doesn't matter, and line 4 states that if two images are dissimilar, they can't both be similar to a third image.

If I and M are represented as point sets, one may first define d as the directed Hausdorff distance from I to M, $$d(I, M) = \sup_{i \in I} \inf_{m \in M} \|i - m\|$$

where $\|\cdot\|$ is a norm (for this paper, it is the $L_2$ (Euclidean) norm). If I and M are compact (which is the case when I and M are represented as pixel arrays), then the equation can be simplified to $$d(I, M) = \max_{i \in I} \min_{m \in M} \|i - m\|$$

To compute d(I,M), scan through each point m∈M, compute the distance to its nearest neighbor i∈I, and then take the maximum of these nearest-neighbor distances. However, this definition of d(I,M) is not a metric: d(I,M) is not symmetric, and d(I,M)=0 does not imply that I=M. We can define a metric by taking the maximum of the directed distances d (I,M) and d(M,I), $$H(I,M)=\max(d(I,M),d(M,I))$$

The function H(I,M) satisfies all the properties of a metric. Unfortunately, it is not useful for applications as it too sensitive to outliers. A single point in M that is far from every point in I means that d(I,M) (the directed distance from I to M) is large, and hence H(I,M) is large. This sensitivity can be addressed by introducing a parameter f that represents a quantile:

$$d^f(I, M) = f^{th}_{i \in I} \min_{m \in M} \|i - m\|$$

Here, the maximum has been replaced with the quantile f: take all the nearest-neighbor distances from M to I, sort them in ascending order, and take the fth quantile of these distances. If f=1, then $d^f(I,M)$=d(I,M). The function $d^f(I,M)$ will be referred to as the partial directed Hausdorff distance from I to M. This modification allows Hausdorff distance computations to ignore the presence of outliers arising from noise, occlusion, etc.

Another concern regarding image matching is that pixels are represented on an integer grid. Hence, in the process of evaluating a transformation τ, transforming M by τ will involve the conversion of floating-point numbers into integers via rounding or truncation which can lead to small perturbations between τ(M) and I, even if τ is the exact transformation. This can be adjusted for by allowing another parameter E which acts as an error margin: one may say that τ maps M into I if $$H_\epsilon^{f,g}(I,\tau(M))=\max(d_f(I,\tau(M)),d^g(\tau(M),I)) \leq \epsilon$$

The parameters f, g, and ε may be all set by the user depending on the accuracy desired and the amount of expected noise/occlusion.

Figure 3:
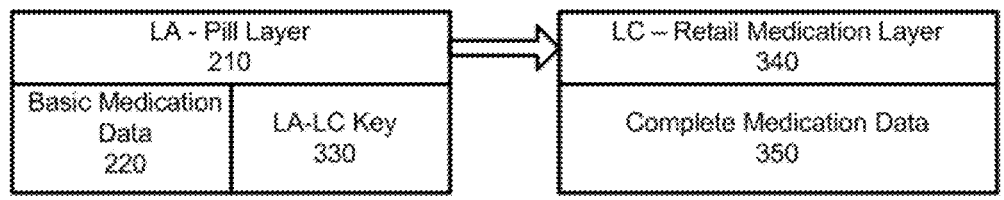
FIG. 3 depicts a third key combination in accordance with an embodiment of the invention.

Computing $d_f(I,\tau(M))$ requires computing the distance from the point τ(m) to its nearest-neighbor i∈I, for all m∈M. This can become computationally expensive very quickly; for example, the 3rd iteration from FIG. 3 was created from a 1024×1024 pixel png image. It contains 676,572 black pixels; 169,143 black pixels in each quadrant. This means that in computing $d^f(I,\tau(M))$ for just one r, for each of the 676,572 black pixels in τ(M) one would have to find the distances to each of the 169,143 pixels in one of the quadrants of I, sort them, and select the minimum inter-point distance as the nearest-neighbor distance. One then would have to sort all the nearest-neighbor distances and select the fth quantile. This is obviously untenable. Hence, one would preferably take a different approach to computing nearest-neighbor distances, as will be described below.

A binary pixel array by convention maps every foreground pixel of an image I to zero and every background pixel to one. A distance transform Δ takes a binary pixel array I and produces an array Δ[I] of the same size where, for each pixel i=($i_x$,$i_y$)=I[x,y],Δ[x,y] represents the distance from i to the closest zero pixel. If I[x,y]=0, then Δ[x,y]=0. The norms used to compute distances are typically $L_1$, $L_2$, and $L_\infty$, also known (respectively) as the Manhattan metric, the Euclidean metric, and the chessboard metric. Distance transforms can be computed quickly and open-source implementations are available.

The relationship between distance transforms and nearest-neighbor distance computation is the following: to find the distance to the nearest-neighbor i∈I for each point m∈M, simply compute Δ[I] and probe it at the locations specified by m=($m_x$,$m_y$)=M [x,y]; since Δ[x,y] represents the distance from I[x,y] to the closest foreground pixel in I, it also represents the distance from M [x,y] to the nearest-neighbor in I.

Since the same Δ[I] can be used to check all transformed models τ(M), it only needs to be computed once, resulting in a significant reduction in the number of computations required.

Distance transforms allow for quickly computing Hausdorff distances between an image I and a transformed model τ(M). However, scanning may still be slowed down by the sheer number of transformations that must be checked. An efficient method for searching through the space of transformations T is required. A hierarchical search method that subdivides T into smaller regions along with a method for evaluating each region to determine if it contains a valid τ is described below.

It was noted above that the transformations T which generate Cantor codes can be represented as vectors $$\tau=[s_x,s_y,t_x,t_y]$$

where the elements are the parameters of the transformation r given as real numbers representing percentages. Since τ will be acting on pixels in image space, it needs to be converted into integer units that represent pixels. The reason for this is that for a given τ, when we compute the Hausdorff distance between τ(M) and I the distance will be measured in pixels. The evaluation method testing a region of T should also result in a value given in pixels. The evaluation method depends on computing norms in T, hence the elements oft need to be parameterized in such a way that a change in one parameter by one unit results in a change of position of τ(M) of at most one pixel. This will allow us to define a norm on T that yields distances in pixel units.

The translational components $\tau_x$ and $\tau_y$ may be expressed as integers e and f, since they simply represent translation in pixels in the x- and y-directions. For $s_x$ and $s_y$, we first need to determine the size of M. For m=($m_x$,$m_y$)∈M, let $M_x$=$\max_{m \in M}$ $m_x$ and $M_y$=$\max_{m \in M}$ $m_y$. Let $s_x$=a/$M_x$ and $s_y$=d/$M_y$, where a and d are integers. Then τ may be rewritten as $$\tau=[a,d,e,f]$$

Let $\hat{\tau}$ be a transformation that differs from τ in only one parameter by only one unit; then $\hat{\tau}$ differs from τ(M) by at most one pixel in one direction. We will refer to a and e as x-linked parameters $\tau_x$, since they cause changes in the x-direction. Similarly, d and f are y-linked parameters $\tau_y$.

Consider a translation t=[$t_x$,$t_y$] and a point m=($m_x$,$m_y$)∈M. Then the distance from m to t(m)=($m_x$+$t_x$,$m_y$+$t_y$) will be $$d = \sqrt{t_x^2 + t_y^2} = \|(t_x, t_y)\|_2.$$

If parameterized scaling's a and d result in changes of τ(M) of at most a and d pixels, then we can extend the norm to $$\|\tau\|_T = \|(\|\tau_x\|_1, \|\tau_y\|_1)_2 = \|(a+e,d+f)\|_2$$

This gives a norm in T that can measures distances between transformations τ(M) and $\hat{\tau}$(M) in pixels.

Now consider a rectilinear region R⊂T that can be expressed as $$R=[a_{min},a_{max}] \times [d_{min},d_{max}] \times [e_{min},e_{max}] \times [f_{min},f_{max}]$$

and the center point of R, $$\tau_c = \left[\frac{a_{min}+a_{max}}{2}, \frac{d_{min}+d_{max}}{2}, \frac{e_{min}+e_{max}}{2}, \frac{f_{min}+f_{max}}{2}\right]$$

Then $$\delta = \left\|\left(\frac{a_{max}-a_{min}}{2}, \frac{d_{max}-d_{min}}{2}, \frac{e_{max}-e_{min}}{2}, \frac{f_{max}-f_{min}}{2}\right)\right\|_{\mathcal{J}}$$

represents the distance from $\tau_c$ to the corners of R. This implies that for $\hat\tau, \tau \in R$, $$|\tau(M)-\hat\tau(M)| \leq \delta$$

i.e., any two transformations in R of M can be at most δ pixels apart. Now, if $$d_f(I,\tau_c(M)) > \epsilon+\delta$$

i.e., the distance from I to $\tau_c(M)$ is greater than $\epsilon+\delta$ pixels, then for every transformation $\tau \in R$, $$d_f(I,\tau(M)) > \epsilon$$

i.e., the distance from I to τ(M) is greater than ε pixels for all τ∈R and we can rule out the entire region R⊂T as not containing a transformation τ within the error margin ε.

This yields an evaluation method: for a rectilinear region R⊂T, compute δ. Evaluate $d_f(I,\tau_c(M))$; if it is greater than ε+δ, one can rule out R from any subsequent searches. This method allows elimination entire regions of transformation space with a single transformation of M and a single partial directed Hausdorff distance computation.

Now that an evaluation method has been defined for ruling out regions R⊂T a method for efficiently subdividing T is desirable so as to minimize the number of transformations τ that need to be evaluated. This method should also decrease the sizes of R so that we are eventually left with regions R that contain a single transformation T.

The simplest approach is to first bound T with min ($s_x$), max($s_x$), ..., min ($t_y$), max ($t_y$). These values may be set by the user when initializing the generation method. Then, for a given M and I, proceeding in an iterative manner, 1) For each region R compute δ. If all regions have the same size and shape, then the same δ can be used for each R.
2) For each region R determine $\tau_c$ and compute $d_f(I,\tau_c(M))$. If $d_f(I,\tau_c(M)) > \epsilon+\delta$, then it cannot contain any transformation x that would bring τ(M) to within εpixels of I, and it can be marked uninteresting. Otherwise, mark R as interesting.
3) Subdivide all R's marked interesting. The simplest approach is to divide the lengths of each side of the rectilinear regions by 2. For a 4-dimensional rectilinear region, this results in $2^4$=16 equal-sized subregions.

Initially, R can be set equal to the entire bounded region of T. Once the side-lengths of each R are 1 (meaning they contain a single transformation), then for each τ we can compute $d^g(\tau(M),I)$ and therefore determine $H_\epsilon^{f,g}(I,\tau(M))$.

Information Capacity Extension—

Figure 15:
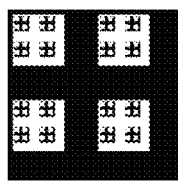
FIG. 15 is a multiple layer Cantor code construction in accordance with an embodiment of the invention.
Figure 15:
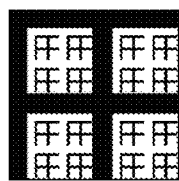
Figure 15:
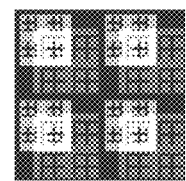

As currently described, Cantor codes allow a limited amount of information to be encoded. For example, as noted above, if each of the 16 parameters in T can take 5 possible values, then the number of contraction mappings is $5^{16}$=152,587,890,625. Hence, 11-digit base-10 numeric codes may be treated as numbers, converted into base-5, and then encoded as the parameters of T. A method to extend the number of digits that may be represented is to layer 2 or more Cantor codes on top of each other, in different colors. Color may be employed as the distinguishing factor, for example. Furthermore, determination of missing or remove pixels may also be employed. Pixels that are common to each Cantor code may be colored a different color from any of the Cantor codes. As long as the colors are easily distinguishable, the combined Cantor code can be separated into layers and each layer treated as a separate Cantor code. FIG. 15 illustrates this method.

Cantor1 is the Cantor code generated by $$T = \begin{pmatrix} 0.30 & 0.30 & 0.03 & 0.03 \\ 0.30 & 0.30 & 0.03 & 0.03 \\ 0.30 & .30 & 0.03 & 0.03 \\ 0.30 & 0.30 & 0.03 & 0.03 \end{pmatrix}$$

while Cantor2 is the Cantor code generated by $$T = \begin{pmatrix} 0.38 & 0.38 & 0.11 & 0.11 \\ 0.38 & 0.38 & 0.11 & 0.11 \\ 0.38 & 0.38 & 0.11 & 0.11 \\ 0.38 & 0.38 & 0.11 & 0.11 \end{pmatrix}$$

Cantor3 is created by layering the image arrays of Cantor1 and Cantor2; dark gray pixels correspond to pixels that are black for both Cantor1 and Cantor2, while white pixels correspond to pixels that are white for both Cantor1 and Cantor2. Two other shades of gray are used to represent pixels that are black for Cantor1 and white for Cantor2 and vice versa.

Figure 16:
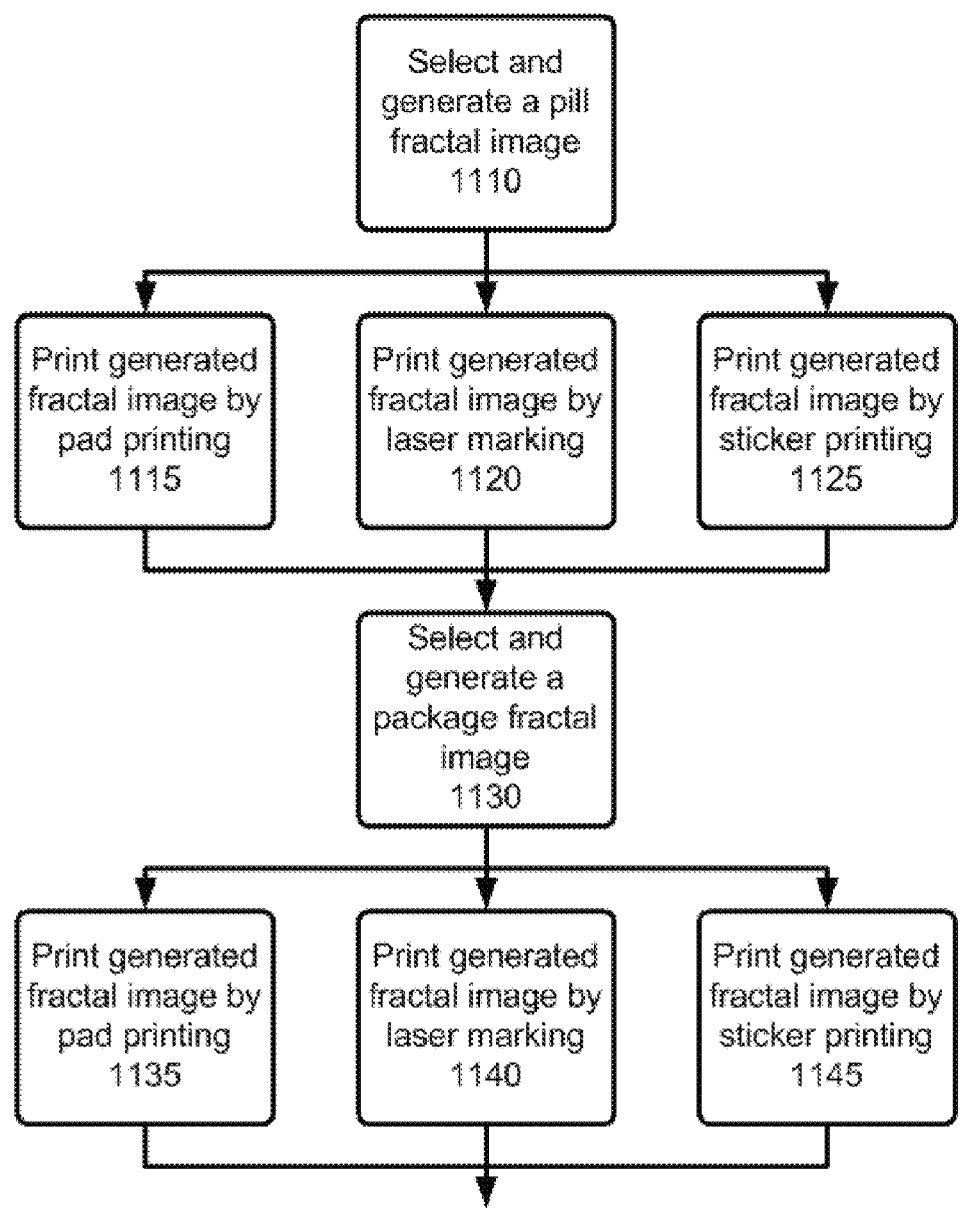
FIG. 16 is a flowchart diagram depicting a method of application of the various elements to printing a desired fractal image to a medication pill in accordance with an embodiment of the invention.
Figure 17:
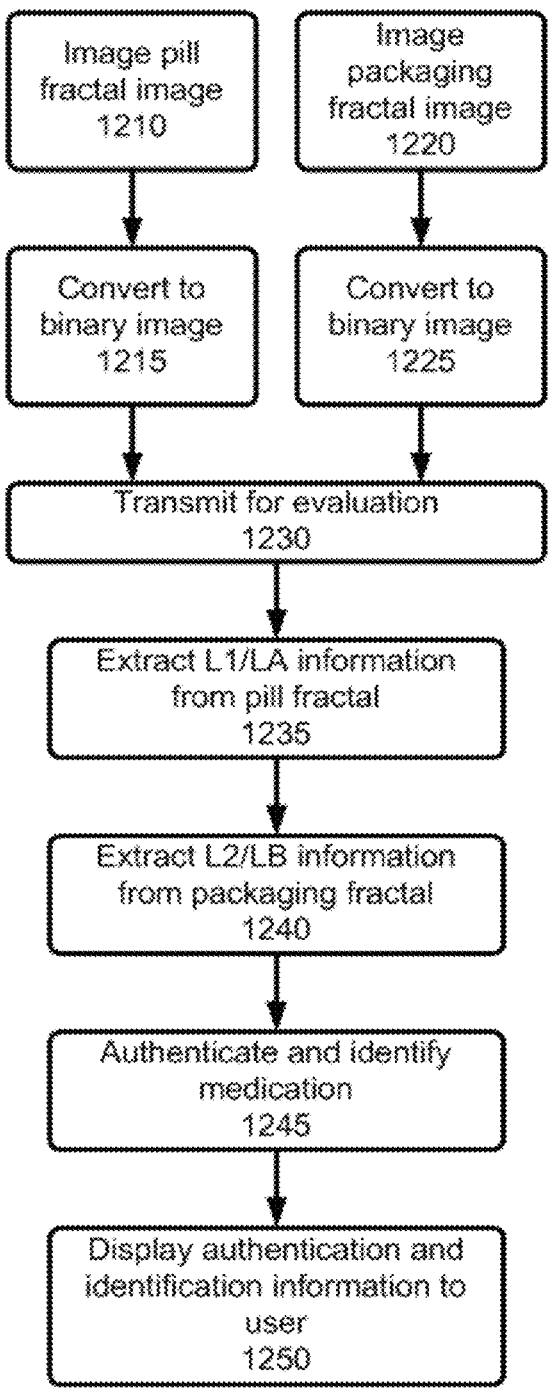
FIG. 17 is a flowchart diagram depicting a method of application of the various elements to the recovery of information from printed fractal images in accordance with an embodiment of the invention.

Referring next to FIGS. 16 and 17, a process for implementation of the printing and scanning authentication and identification techniques, employing one or more of the fractal library components described above, will now be described. As is shown in FIG. 16, at step 1110 a fractal image to be printed to a medication pill is selected and generated. Such image is preferably generated in accordance with one or more of the fractal library generation techniques described above, and preferably includes encoded information noted in a pill fractal image, such as basic medication information and an L1-L2 or LA-LB key, depending on the distribution method, as described above. Next at steps 1115, 1120, and 1125, such a fractal image is printed to a medication pill, using one of the respective techniques of pad printing, laser marking and sticker printing. Next (or in parallel to, or even before), a fractal image may be selected and generated to be used on appropriate packaging at step 1130. Information encoded in this fractal preferably varies depending on the location of the fractal image, such as on a box including blister-packed medication, a wholesale container, or a retail container, as described above. Once generated, then one or more of the printing techniques, or other appropriate printing technique, may be employed at steps 1135, 1140, 1145 to print the image to the appropriate packaging.

Once distributed, processing then passes to FIG. 17 in which a fractal image from a pill is first imaged at step 1210, including the processes of correcting the image to account for any lighting or noise issues, and further may include white balancing, grey scaling and the like. Such imaging may employ a camera on a standard mobile device, a common camera or other imaging device, a high powered imaging device, or a purpose-made imaging device and apparatus. Then at step 1215, this image is preferably converted to a binary image (and indeed, some or all of the processes described in step 1210 may be considered as part of the conversion to a binary image), although such conversion may be omitted if desired. At step 1220, either before, after or in parallel with the imaging of the pill fractal image, the packaging fractal image is preferably imaged as well, using similar techniques as noted above for the pill fractal image, and is then similarly converted to a binary image at step 1230. Such transmission may be to a remote cloud based location for processing, but may comprise any desirable processing location, maintained on a computer network or the like. In an alternative embodiment, it is possible to have adequate processing hardware and software locally to perform such processing without transmission of the images.

Once received at the processing location, the pill fractal image is decoded at step 1235 where L1 or LA lock information is preferably extracted, in addition to the basic pill information. This decoding may employ one or more of the techniques noted above, and may employ a process for transforming a known code and an imaged code a number of times, and then computing a Hausdorff distance between the resulting transformed images, as noted above (an as is further described below). Next, at step 1240, this extracted information may be used as a key to unlock the L2/LB information encoded in the packaging fractal image. Once unlocked, the L1/LA and L2/LB information may be used to authenticate and identify the medication. Of course, one or the other may be used alone, or both be employed for such identification and authentication.

Once authenticated, this authentication confirmation and medication identifying information is preferably transmitted to the user (on their mobile device, computer, or other communication device, for display and their user at step 1250. Thus, the user is quickly provided with a confirmation of the authenticity of the medication as well as identifying information. It should be noted that the packaging information described above may be any of the packaging information described above with respect to the different medication distribution and use methods.

Once authenticated, the identification process described above (employing pill-only imaging and identification) may preferably be employed for future identification of correct medication. Such identification may be part of an automated adherence monitoring system employing computer vision or the like to automatically confirm the identity of medication, and that the user has properly ingested or otherwise administered their medication pills.

The process of recovering the parameters of the affine maps from an image of a Cantor code (or other employed fractal or fractal-like image) preferably requires accurately determining the location of the Cantor code inside the image. Since Cantor codes are square regions, locating them may be accomplished by looking for their square borders in the image. The problem of locating squares may be reduced to looking for pairs of parallel lines that are orthogonal and equidistant. The following method (described initially referring to FIG. 18) may be used to detect squares and determine if the Cantor code is contained within them. It has the advantage of being rotation invariant—Cantor codes at any alignment within the image may be detected.

Figure 18:
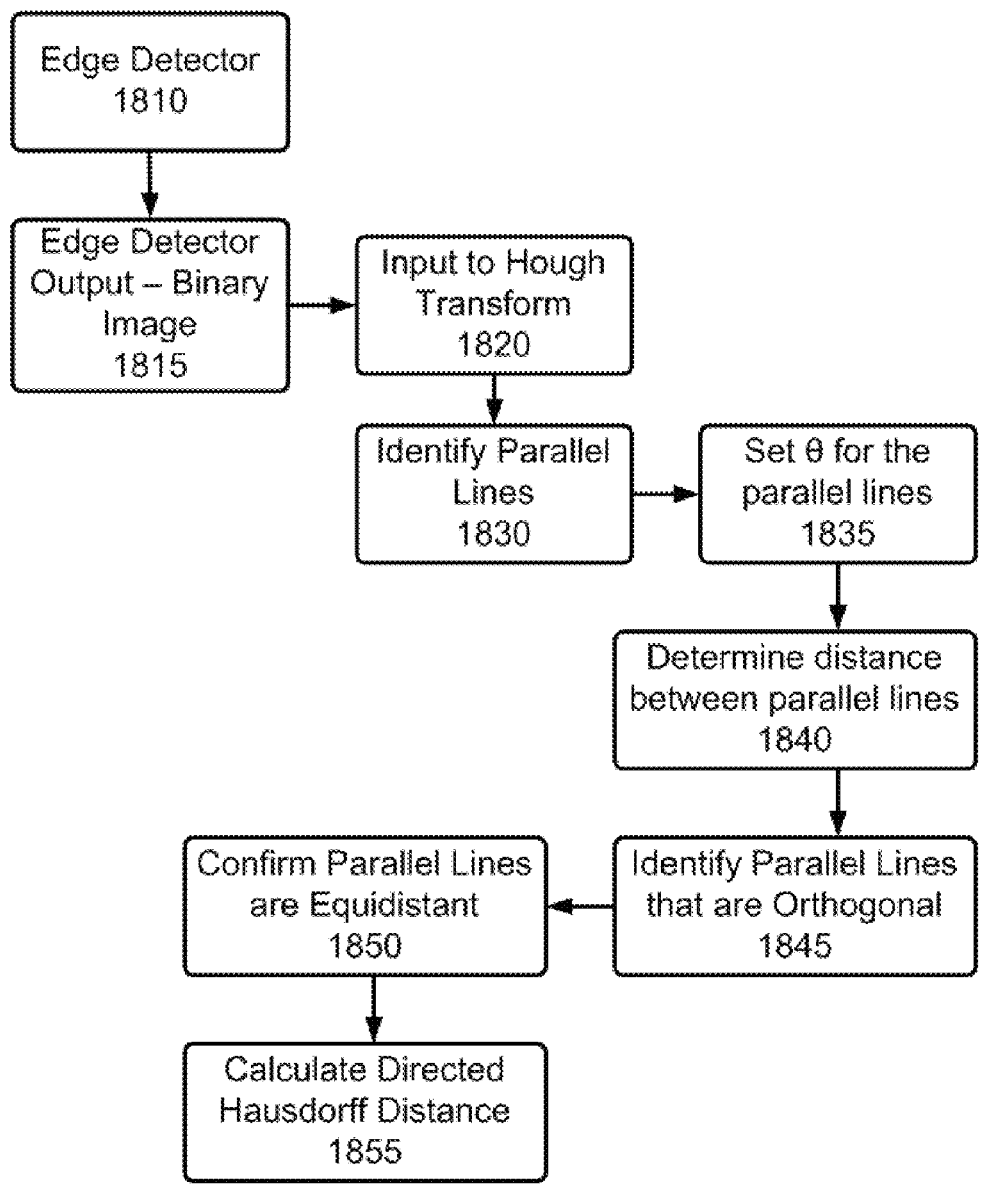
FIG. 18 depicts a process for recognizing an inventive Cantor code in accordance with an embodiment of the invention.

As will be described with respect to FIGS. 18 and 19, the process of recovering the parameters of the affine maps from an image of a Cantor code produced in accordance with one or more embodiments of the invention requires accurately determining the location of the Cantor code inside the image. Since Cantor codes are square regions, the inventors of the present invention have determined that locating them may be accomplished by looking for their square borders in an image. The problem of locating squares may be reduced to looking for pairs of parallel lines that are orthogonal and equidistant. The following method shown in FIG. 18 may be used to detect squares and determine if the Cantor code is contained within them. It has the advantage of being rotation invariant—Cantor codes at any alignment within the image may be detected.

First, at step 1810, an edge detector is preferably used to find the edges of the Cantor code in the image. Such an image in accordance with various embodiments of the invention may be provided on a medication pill, for example, as shown in FIG. 19(*a*). Any edge detector, such as Canny, Sobel, or Prewitt, may be used. The output of edge detectors provided at step 1815 is a binary image, where pixels are marked as either edge or non-edge pixels, as shown in FIG. 19(*b*). This binary image is then used as the input to the Hough transform at step 1820. The Hough transform is a shape detector that can detect lines described in parametric form, $$x \cos \theta + y \sin \theta = \rho$$

where $\rho$ is the length of a normal from the origin to the line and $\theta$ is the orientation of r with respect to the origin. Since the process is looking for a square region, it can begin by identifying pairs of parallel lines in step 1830, as shown in FIG. 19(*c*). In parametric form, parallel lines will have the same value of $\theta$. Due to discretization, parallel lines in an image may not have exactly equal values of $\theta$; this can be addressed by introducing a threshold $\theta_\|$. Therefore, two lines a, b, with parameters $(\rho_a, \theta_a)$ and $(\rho_b, \theta_b)$ are considered parallel if $$|\theta_a - \theta_b| < \theta_\|$$

One then sets $\theta$ for a pair of parallel lines (a,b) as $\theta_{a,b} = \frac{1}{2}(\theta_a + \theta_b)$ at step 1835. One may also record the distance between the parallel lines at step 1840. For a pair of parallel lines a, b, with parameters $(\rho_a, \theta_a)$ and $(\rho_b, \theta_b)$, the distance $\delta_{a,b}$ between them is given by $$\delta_{a,b} = |\rho_a - \rho_b|$$

Figure 19:
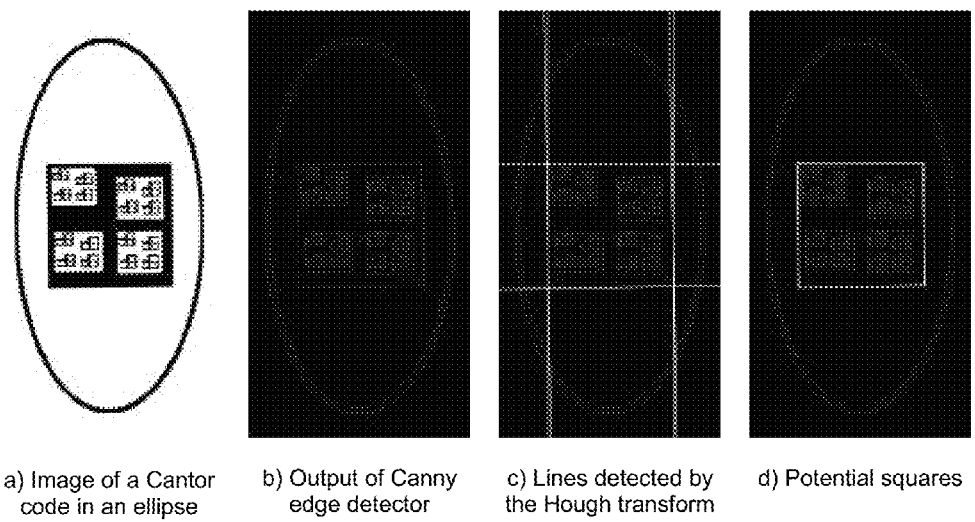
FIG. 19 depicts determination of location of a potential Cantor code in accordance with an embodiment of the invention.

After pairs of parallel lines have been identified, one may identify potential squares by identifying pairs of parallel lines that are orthogonal and equidistant at step 845, as shown in FIG. 19(*d*). In parametric form, orthogonal lines will have values of $\theta$ that differ by $\pi/2$ radians. Given pairs of parallel lines a, b, and c, d, with parameters $\theta_{a,b}$ and $\theta_{c,d}$ and a threshold $\theta_\perp$, the pairs are considered orthogonal if $$\left||\theta_{a,b} - \theta_{c,d}| - \theta_\perp\right| < \frac{\pi}{2}$$

i.e., the angle between the pairs of parallel lines is within a threshold value of $\pi/2$ radians, or 90 degrees. In addition to the orthogonality requirement, one may also require that the pairs of parallel lines be equidistant at step 1850, thus further ensuring a square. Given pairs of parallel lines a, b, and c, d, with distances $\delta_{a,b}$ and $\delta_{c,d}$ and a threshold $\delta_\tau$, the pairs are considered equidistant if $$\left|1 - \frac{\delta_{a,b}}{\delta_{c,d}}\right| < \delta_\tau$$

or $$|\delta_{a,b} - \delta_{c,d}| < \delta_\tau$$

depending on whether one wishes to compare the ratios of distances or the difference of distances in pixel units, wither of which may be employed in accordance with one or more embodiments of the invention. The lines detected by the Hough transform in accordance with the embodiments of the invention have resulted in two potential squares in FIG. 19(*d*).

As FIG. 19 illustrates, the process of identifying the square border of a Cantor code in accordance with one or more embodiments of the invention may yield multiple potential squares that vary slightly. Also, the Hough transform may pick up false lines, resulting in false squares. In order to differentiate between potential squares and eliminate false squares, in accordance with an embodiment of the invention, the directed Hausdorff distances may be calculated from the potential/false squares to the edge image. The potential square that is best located and aligned with the border of the Cantor code will have the smallest directed Hausdorff distance.

Figure 20:
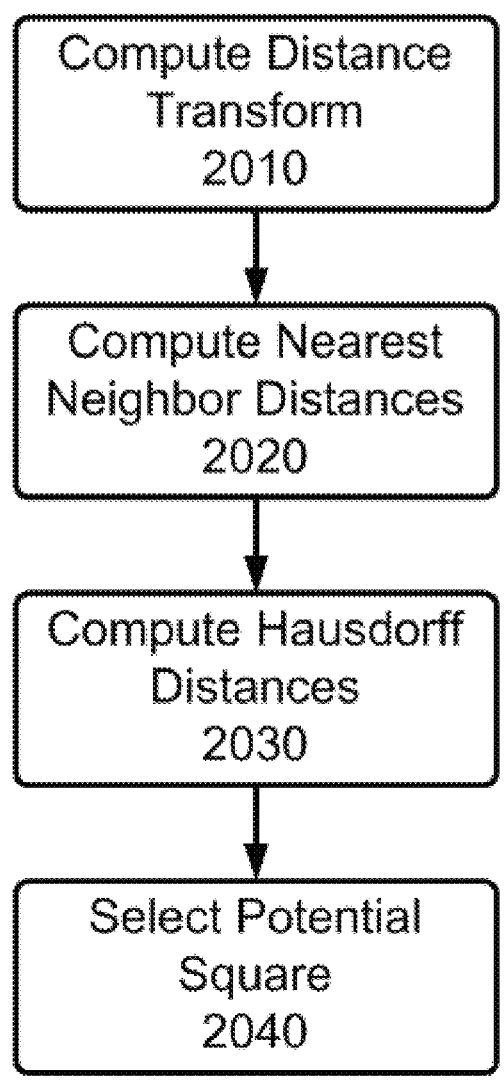
FIG. 20 depicts a method for selecting one or more possible Cantor codes in accordance with an embodiment of the invention.

This may be accomplished in accordance with the method as shown in FIG. 20. First, at step 2010 a distance transform of the edge image is first computed. Then, at step 2020 for each potential square, nearest-neighbor distances to the edge image for each pixel are computed in the potential square using the distance transform. These distances may then be used in step 2030 to compute Hausdorff distances, and select the potential square in step 2040 with the smallest Hausdorff distance as the best-matching square.

Figure 21:
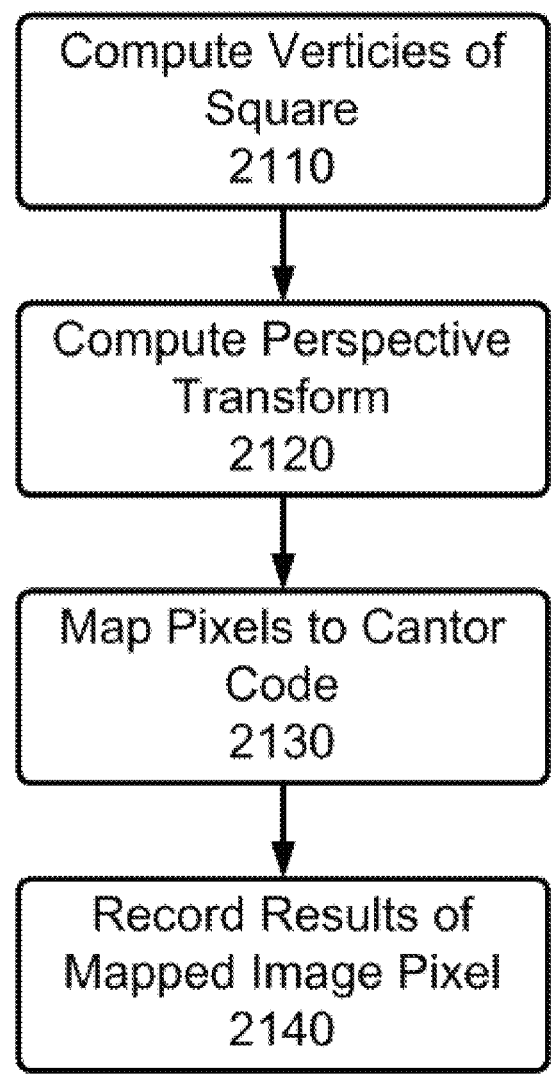
FIG. 21 depicts a further method for aiding in selecting one or more Cantor codes in accordance with an embodiment of the invention.

Once one knows the location of the border of the Cantor code, one can extract the Cantor code from the image. As is shown in FIG. 21, one may first compute, at step 2110, the vertices of the square, which are defined as the intersections of the lines that comprise the square border. Using the parametric form of the lines, the intersection of two lines defined by $(\rho_a, \theta_a)$ and $(\rho_b, \theta_b)$ is the point (x,y) that satisfies the pair of equations $$x \cos \theta_a + y \sin \theta_a = \rho_a$$

$$x \cos \theta_b + y \sin \theta_b = \rho_b$$

There are two equations in two unknowns; x and y can be computed by solving the linear system. Once all four vertices have been computed, the perspective transform from a square array to the border of the Cantor code may then be computed in step 2120. Perspective transforms map arbitrary quadrilaterals to arbitrary quadrilaterals. This is done for two reasons:
1) The border that has been detected may not be perfectly square, due to distortions in the image and/or discretization of the image into pixel coordinates.
2) The border may not be perfectly upright; therefore one cannot simply crop the image to extract the Cantor code.

The inventors of the present invention have determined that this last point is especially relevant when an image of a Cantor code is taken by a person holding an object which has a Cantor code printed on it; it's difficult for a person to hold an object in such a way that the Cantor code is perfectly aligned.

Figure 22:
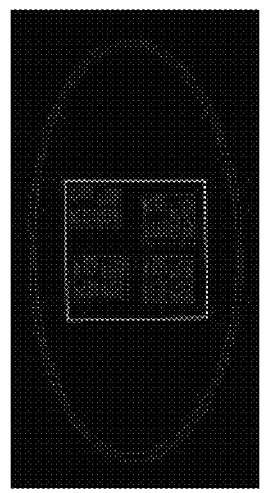
FIG. 22 depicts a result of the processing for determining a possible Cantor code in accordance with an embodiment of the invention.
Figure 22:
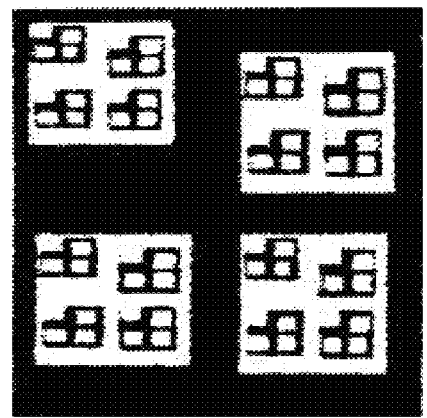

Once the perspective transform has been computed, at step 2130 it can be used to map each pixel in a square array of the same size (defined as the area of the quadrilateral defined by the border of the Cantor code) as the Cantor code to its corresponding pixel in the image of the Cantor code, and record the results of the mapped image pixel in the square array. FIG. 22(a) illustrates a Cantor code that has been segmented from an image using this process after the best-matching square border was detected, while FIG. 22(b) shows Cantor codes ready for scanning.

The inventors of the present invention have determined that the multi-resolution technique previously described may result in long processing times, as more searches may be performed than during an exhaustive search if transformations result in images that are too close together. In addition, transforming every pixel of an image of a Cantor code during each search can be extremely time-consuming. An exhaustive search may be conducted in a reasonable amount of time if edge images are used instead of an entire Cantor code.

Therefore, in accordance with one or more embodiments of the invention, after the Cantor code has been segmented from an image using the method described above, an edge detector may be used to extract the edges within the Cantor code. The reduction in pixels that must be transformed can be quite large. For example, image 23(a) is 662×662 pixels; it contains 414,947 black pixels. Image 23(b) is the output of the Canny edge detector; it contains 16,881 edge pixels, a reduction of 96%.

After computing the pixel coordinates of the edge pixels, an exhaustive search through all possible transformations for each quadrant may be conducted. The quadrants may comprise any portion of any sized code matrix, such as 2×2, 3×3, etc. The quadrants of the image are preferably scanned sequentially; for each quadrant, and for each possible transformation, the edge pixels of the entire Cantor code are transformed. The directed Hausdorff distance from the transformed edge pixels to the edge pixels of the current quadrant of the Cantor code is computed using the distance transform of the Cantor code edge pixels. If the directed Hausdorff distance is below a user-defined threshold (for example, half of the distance between allowed parameters times the size of the Cantor code), then the directed Hausdorff distance from the Cantor code edge pixels to the transformed edge pixels may be computed.

Figure 23:
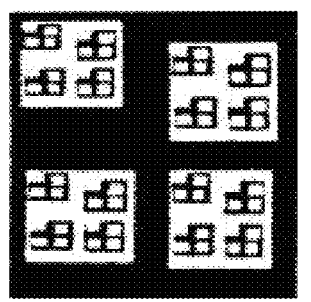
FIG. 23 depicts an edge image of a determined Cantor code in accordance with an embodiment of the invention.
Figure 23:
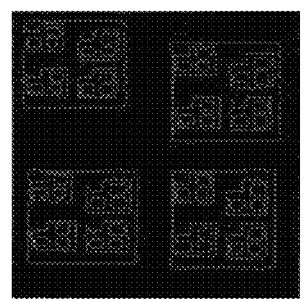
Figure 24:
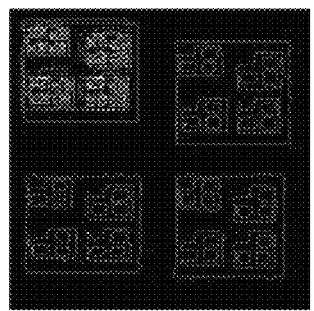
FIG. 24 is a depiction of employment of correct and incorrect affine or other transformations in accordance with an embodiment of the invention.
Figure 24:
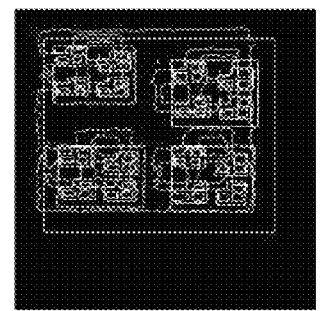
Figure 24:
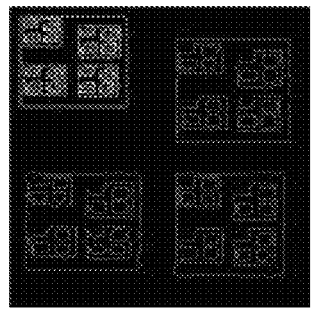
Figure 24:
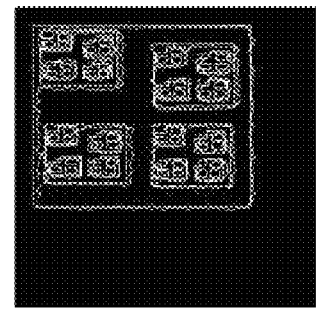

FIG. 24 illustrates how individual transformations are tested. The edge pixels of the entire Cantor code may be transformed by two different transformations. The first transformation was off by one value for each parameter, while the second transformation used the correct parameters. The images demonstrate the differences in the transformations which will be reflected in the directed Hausdorff distances. FIG. 24 presents an illustration of search for correct affine transformations of a Cantor code. In FIG. 24(a) the Cantor code was transformed by an incorrect affine transformation for the 1st quadrant; FIG. 23(b) is a close-up of the 1st quadrant. In FIG. 23(c) the Cantor code was transformed by the correct affine transformation for the 1st quadrant; FIG. 23(d) is a close-up of the 1st quadrant. The affine transformation used in images 23(c) and 23(d) mapped the Cantor code to itself much more accurately than the affine transformation used in images 23(a) and 23(b); this difference will be reflected in the Hausdorff distance calculations, and therefore, the image in FIGS. 23(c) and 23(d) will be considered the "correct" mappings.

Figure 25:
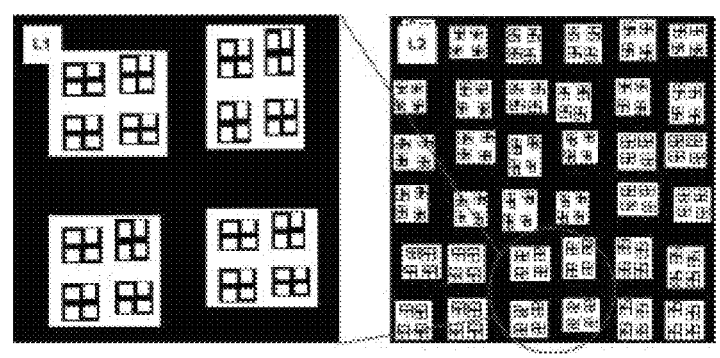
FIG. 25 depicts the inclusion of geographical data for a portion of a Cantor code within the cantor code in accordance with an embodiment of the invention.

Therefore, in this manner, a match of an imaged cantor code and a desired Cantor code may be determined, allowing for the recovery of information from the medication pill. When employed on medication pills and/or packaging of one kind or another, various additional relationships between the employed fractal images may be considered. As is shown in FIG. 25, The L2 fractal cluster may contains as one of its elements the L1 fractal. L1 fractal encodes (in addition to the basic medication data) a pointer to its location on L2 fractal, thus providing the necessary encrypted correlation key between the two. L2 fractal contains the complete medication data and the one-time code used for authentication. In such a manner, information encoded in the Cantor codes may be utilized in extracting the data therefrom.

It is therefore contemplated in accordance with the various embodiments of the invention to provide a robust system for authenticating and identifying medication pills, other medication, or objects in general using a two layer imaged based system. The inherent high geometrical complexity and self-similarity of high resolution, multi-iteration fractals (or other images displaying fractal-like qualities) will make them highly immune to copying. By cross-comparing several fractal iterations one will be able to verify authenticity. Low quality copied fractal images will fail this test. More complex fractal or fractal-like images may be employed at one or more iterations to increase robustness to copying.

It is contemplated that the invention be applicable to other types of images, such as those displaying fractal-like qualities, or other complex images making copying difficult. It is further contemplated that any local imaging device used by a user further comprises sufficient processing hardware, software, memory, and data transmission and receiving system to allow for performance of the features noted herein. It is further contemplated that any remote or local processing computer has sufficient processing hardware, software, memory and data transmission and receiving system to perform the features noted herein, and including the decoding of fractal images.

Imaging devices for imaging the various codes may include mobile device cameras, microscopes, scanners and the like. Processors may be positioned locally or remotely, and may comprise any necessary computing and storage components, including storage devices, input output ports displays, computer processors and software algorithms or programs to operate the processors.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A method for authenticating medication, comprising generating a first recoverable key and a second recoverable key;
    printing the first recoverable key on a medication pill; and
    printing the second recoverable key on a medication packaging for the medication pill,
    wherein at least a portion of the first recoverable key is configured to extract information from the second recoverable key, the information from the second recoverable key comprising medication authentication information,
    wherein generating the first recoverable key and/or the second recoverable key comprises:
    (a) defining an initial shape;
    (b) applying one or more transformations to the initial shape to generate one or more transformed shapes;
    (c) modifying one or more characteristics of the one or more transformed shapes; and
    (d) layering one or more of the one or more transformed shapes on the initial shape to provide a layered image corresponding to the first recoverable key or the second recoverable key,
    wherein a plurality of parameters associated with a function characterizing the layered image are extractable from the layered image and encode medication information.

2. The method of claim 1, wherein one or more of the first recoverable key and the second recoverable key comprises an image having one or more fractal properties.

3. The method of claim 2, wherein one or more of the one or more first recoverable key and second recoverable key comprises a fractal-like image employing one or more Cantor codes.

4. The method of claim 3, wherein one or more pieces of information that may be extracted from the first recoverable key indicate a location of one or more pieces of information in the second recoverable key.

5. The method of claim 1, wherein the first recoverable key comprises basic medication information and a key for linking the first recoverable key and the second recoverable key.

6. The method of claim 1, wherein the second recoverable key comprises medication information and the medication authentication information comprises a one-time code.

7. The method of claim 6, wherein the one time code is configured to provide a one-time confirmation of medication authentication from an authentication processor.

8. The method of claim 7, wherein the authentication processor is located at a remote location.

9. The method of claim 1, wherein the plurality of parameters are coefficients of a polynomial.

10. The method of claim 9, wherein the plurality of parameters comprise coefficients of affine transformations.

11. A method for providing an identification key, comprising the steps of:
    (a) defining an initial shape;
    (b) applying one or more transformations to the initial shape to generate one or more transformed shapes;
    (c) modifying one or more characteristics of the one or more transformed shapes; and
    (d) layering one or more of the one or more transformed shapes on the initial shape,
    wherein the initial shape and the one or more layered transformed shapes comprise the identification key, and
    wherein a plurality of parameters associated with a function characterizing the identification key are extractable from the identification key and encode identification information.

12. The method of claim 11, further comprising:
    (e) defining the identification key as the initial shape; and
    (f) repeating (b)-(d) a predetermined number of times to generate an identification key with a predetermined number of layers.

13. The method of claim 11, wherein the initial shape is a square.

14. The method of claim 13, wherein four transformations are applied to the initial shape to generate four transformed shapes.

15. The method of claim 14, wherein each of the four transformed shapes is placed in a quadrant of the initial shape.

16. The method of claim 13, further comprising:
    changing a color of each of the four transformed shapes; and
    placing one or more of the four transformed shapes in a quadrant of the initial shape.

17. The method of claim 11, wherein the initial shape is a solid shape.

18. The method of claim 11, wherein the transformation transforms one or more of size, location, rotation and reflection.

19. A method for recovering a medication key, comprising:
    imaging the medication key employing an imaging device, the medication key being formed in accordance with:
    (a) defining an initial shape;
    (b) applying one or more transformations to the initial shape to generate one or more transformed shapes;

(c) modifying one or more characteristics of the one or more transformed shapes; and (d) layering one or more of the one or more transformed shapes on the initial shape to provide the medication key; and extracting a plurality of parameters from the imaged medication key, wherein the plurality of parameters encode identification information and are associated with a function characterizing at least a portion of the imaged medication key.

20. The method of claim 19, wherein extracting the one or more parameters from the imaged medication key comprises:

determining one or more edges located within the imaged medication key;

identifying one or more pairs of parallel lines from among the one or more determined edges;

identifying one or more squares comprising one or more outer edges of a key candidate;

defining a perspective transformation in accordance with the identified outer edges of the key candidate;

applying the perspective transformation to the key candidate to generate the medication key; and scanning the medication key to find one or more transformed versions of the medication key therein.

21. The method of claim 20, wherein scanning further comprises:

defining a plurality of transformations to be applied to the medication key;

applying one or more of the plurality of transformations to the medication key to generate one or more transformed medication keys;

comparing one or more of the one or more transformed medication keys to the medication key by performing a Hausdorff distance calculation therebetween; and selecting a best match having a lowest Hausdorff distance.

22. The method of claim 19, wherein the one or more transformations are generated in accordance with one or more pieces of information to be encoded.

23. The method of claim 19, wherein extracting the plurality of parameters comprises:

obtaining a first image and a second image from the imaged medication key;

applying a transformation function to the second image;

determining that a distance between the first image and the transformed image is within a pre-specified range; and designating coefficients of the transformation function as the plurality of parameters.

\* \* \* \* \*